US012596123B2

(12) United States Patent
Nakamura et al.

(10) Patent No.: US 12,596,123 B2
(45) Date of Patent: Apr. 7, 2026

(54) INFORMATION PROCESSING APPARATUS, BIOLOGICAL SPECIMEN ANALYSIS METHOD, BIOLOGICAL SPECIMEN DETECTION APPARATUS, AND BIOLOGICAL SPECIMEN DETECTION SYSTEM

(71) Applicant: Sony Group Corporation, Tokyo (JP)

(72) Inventors: Tomohiko Nakamura, Tokyo (JP); Kazuhiro Nakagawa, Saitama (JP)

(73) Assignee: Sony Group Corporation, Tokyo (JP)

( * ) Notice: Subject to any disclaimer, the term of this patent is extended or adjusted under 35 U.S.C. 154(b) by 631 days.

(21) Appl. No.: 17/927,333

(22) PCT Filed: May 28, 2021

(86) PCT No.: PCT/JP2021/020531
§ 371 (c)(1),
(2) Date: Nov. 22, 2022

(87) PCT Pub. No.: WO2021/241757
PCT Pub. Date: Dec. 2, 2021

(65) Prior Publication Data
US 2023/0288427 A1 Sep. 14, 2023

(30) Foreign Application Priority Data

May 29, 2020 (JP) ................................. 2020-094733

(51) Int. Cl.
| | |
|---|---|
| *G01N 33/58* | (2006.01) |
| *B01L 3/00* | (2006.01) |
| *G01N 21/64* | (2006.01) |

(52) U.S. Cl.
CPC ...... *G01N 33/582* (2013.01); *B01L 3/502715* (2013.01); *G01N 21/6428* (2013.01);
(Continued)

(58) Field of Classification Search
CPC ............ G01N 33/582; G01N 21/6428; G01N 2021/6439; G01N 33/58; G01N 33/5302;
(Continued)

(56) References Cited

U.S. PATENT DOCUMENTS

| | | | |
|---|---|---|---|
| 8,731,844 | B2 | 5/2014 | Herzenberg et al. |
| 2006/0269970 | A1 | 11/2006 | Paul |
| 2014/0170678 | A1 | 6/2014 | Kasdan |

FOREIGN PATENT DOCUMENTS

| | | |
|---|---|---|
| CN | 102388306 A | 3/2012 |
| CN | 105300938 A | 2/2016 |

(Continued)

OTHER PUBLICATIONS

International Written Opinion and English translation thereof mailed Jul. 20, 2021 in connection with International Application No. PCT/JP2021/020531.

(Continued)

*Primary Examiner* — Samuel P Siefke
(74) *Attorney, Agent, or Firm* — Wolf, Greenfield & Sacks, P.C.

(57) ABSTRACT

To provide a technique for supporting selection of a binding molecule and a labeled molecule to be used in detecting and/or analyzing a target molecule. An information processing apparatus, including:
a processing unit configured to calculate, based on a signal derived from a sample including a biological specimen, when using a plurality of different binding molecules labeled by different labeled molecules, reactivity between a target molecule and each of the plurality of different binding molecules,
wherein
the signal includes:

(Continued)

a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule.

15 Claims, 16 Drawing Sheets

(52) U.S. Cl.
CPC ...  *B01L 2200/16* (2013.01); *B01L 2300/0654* (2013.01); *G01N 2021/6439* (2013.01)

(58) Field of Classification Search
CPC ........... B01L 3/502715; B01L 2200/16; B01L 2300/0654
See application file for complete search history.

(56) References Cited

FOREIGN PATENT DOCUMENTS

| | | | |
|---|---|---|---|
| CN | 109477834 | A | 3/2019 |
| CN | 110178013 | A | 8/2019 |
| EP | 3124969 | A1 | 2/2017 |
| GB | 2563254 | A | 12/2018 |
| JP | 2014-206551 | A | 10/2014 |
| WO | WO-2005119258 | A1 | 12/2005 |
| WO | WO 2014/144826 | A1 | 9/2014 |

OTHER PUBLICATIONS

International Preliminary Report on Patentability and English translation thereof mailed Dec. 8, 2022 in connection with International Application No. PCT/JP2021/020531.

Extended European Search Report issued Nov. 8, 2023 in connection with European Application No. 21812416.2.

PCT/JP2021/020531, Jul. 20, 2021, International Search Report.

International Search Report and English translation thereof mailed Jul. 20, 2021 in connection with International Application No. PCT/JP2021/020531.

AF555CD3

AF555 CHANNEL (NEGATIVE CONTROL)

AF647CD5

AF647 CHANNEL (NEGATIVE CONTROL)

INFORMATION PROCESSING APPARATUS, BIOLOGICAL SPECIMEN ANALYSIS METHOD, BIOLOGICAL SPECIMEN DETECTION APPARATUS, AND BIOLOGICAL SPECIMEN DETECTION SYSTEM

CROSS-REFERENCE TO RELATED APPLICATIONS

This application claims the benefit under 35 U.S.C. § 371 as a U.S. National Stage Entry of International Application No. PCT/JP2021/020531, filed in the Japanese Patent Office as a Receiving Office on May 28, 2021, which claims priority to Japanese Patent Application Number JP2020-094733, filed in the Japanese Patent Office on May 29, 2020, each of which is hereby incorporated by reference in its entirety.

TECHNICAL FIELD

The present technique relates to an information processing apparatus. More specifically, the present technique relates to an information processing apparatus, a biological specimen analysis method, a biological specimen detection apparatus, and a biological specimen detection system to be used when detecting a biological specimen.

BACKGROUND ART

Various analyses using labels are being performed in order to analyze various molecules. For example, molecules such as antigenic proteins are being detected and/or analyzed through a flow cytometer or a microscope using an antibody labeled with a plurality of fluorochromes. In addition, besides antigen-antibody reactions, detection and analysis of molecules by nucleic acid hybridization using a fluorescently-labeled nucleic-acid probe and detection and analysis of enzyme molecules using a fluorescently-labeled substrate are being widely performed. Various fluorochromes are used in these detections and/or analyses. Each fluorochrome has unique characteristics such as a unique fluorescence spectrum, fluorescence intensity, and the like.

For example, PTL 1 describes an invention related to a technique for analyzing a kind of fluorescence emitted from a microparticle, and the like (Paragraph 0001). PTL 1 below describes "A data displaying method, comprising: obtaining detected data by simultaneously detecting, in a plurality of wavelength regions, fluorescence generated from a microparticle flowing through a channel; and displaying a fluorescence spectrum obtained by accumulating or averaging pieces of the detected data corresponding to a plurality of the microparticles" (claim 1).

In addition, PTL 2 describes a method of presenting combinations of fluorochromes and antibodies, nucleic acid probes, and the like which bind to antigens, nucleic acids, and the like.

CITATION LIST

Patent Literature

[PTL 1]
JP 2014-206551A
[PTL 2]
U.S. Patent Specification No. 8731844

SUMMARY

Technical Problem

When a binding molecule such as an antibody or a nucleic acid probe is reacted with a target molecule such as an antigen or a nucleic acid, reactivity differs depending on a type of the target molecule or the binding molecule. In addition, the reactivity of the binding molecule with respect to the target molecule also differs depending on a type of a labeled molecule such as fluorescence that labels the binding molecule. Therefore, the type of a binding molecule or a labeled molecule used in order to detect a target molecule also affects detection accuracy.

A binding molecule and a labeled molecule must be selected in order to perform detection and/or analysis of a target molecule. While the selection of a binding molecule and a labeled molecule is usually performed by a user himself/herself who is to perform the detection and/or the analysis, this is a time-consuming task, even for an experienced user. In addition, there may be cases where the selected binding molecule and labeled molecule are not suitable for the detection and/or the analysis of the target molecule.

PTL 2 proposes a method of carrying out an evaluation based on measured autofluorescence and single fluorescent staining and presenting a combination of fluorochromes. However, in this case, a signal of a fluorescently-labeled antibody to be an object must be actually measured using the actual fluorescently-labeled antibody to be the object, and signal data of an antibody labeled with another fluorochrome cannot be accurately calculated based on signal data of the antibody labeled with another fluorochrome. In other words, PTL 2 does not describe a method of calculating an unmeasured fluorescently-labeled antibody.

In consideration thereof, a main object of the present technique is to provide a technique for supporting selection of a binding molecule and a labeled molecule to be used in detection and/or analysis of a target molecule.

Solution to Problem

In the present technique, first, an information processing apparatus is provided which includes
  a processing unit configured to calculate, based on a signal derived from a sample including a biological specimen, when using a plurality of different binding molecules labeled by different labeled molecules, reactivity between a target molecule and each of the plurality of different binding molecules,
  wherein
  the signal includes
  a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule.

In the information processing apparatus according to the present technique, as an index of the reactivity, the number of binding molecules and/or a fluorescence intensity labeled by the number of binding molecules can be calculated.

In this case, the fluorescence intensity can be calculated from one or more numerical values selected from an excitation efficiency, a quantum yield, an absorption efficiency, and a ratio of fluorescence labeling (F/P value).

In the present technique, the signal can include at least one of a signal, a specific signal/background, and a specific signal/non-specific signal.

The processing unit of the information processing apparatus according to the present technique can be configured to calculate a background in each detection channel based on a third signal acquired when using negative control on a target molecule.

The processing unit of the information processing apparatus according to the present technique can be configured to calculate a leakage of an autofluorescence signal and/or a leakage of a signal derived from another labeled molecule.

The processing unit of the information processing apparatus according to the present technique can be configured to calculate reactivity with a target molecule with respect to a combination of a labeled molecule and a binding molecule of which a measurement has not been actually performed.

The processing unit of the information processing apparatus according to the present technique can also be configured to select a combination of a labeled molecule and a binding molecule of which the specific signal/background equals or exceeds a threshold.

The processing unit of the information processing apparatus according to the present technique can also be configured to select a combination of a labeled molecule and a binding molecule which maximizes a sum of the specific signal/background.

The processing unit of the information processing apparatus according to the present technique can also be configured to select a combination of a labeled molecule and a binding molecule which maximizes a sum of differences between a signal of the fluorescence intensity and a background of the fluorescence intensity.

The processing unit of the information processing apparatus according to the present technique can also be configured to select a combination of a labeled molecule and a binding molecule based on a magnitude of a signal of fluorescence intensity.

The processing unit of the information processing apparatus according to the present technique can also be configured to select a combination of a labeled molecule and a binding molecule so that labels are to be assigned in a descending order of a signal of fluorescence intensity to binding molecules in an ascending order of a value of the first signal group.

The processing unit of the information processing apparatus according to the present technique can also be configured to select a combination of a labeled molecule and a binding molecule so that labels are to be assigned in an ascending order of a length of a detection wavelength to binding molecules in a descending order of a value of the first signal group.

The information processing apparatus according to the present technique can further include a presenting unit configured to present, to a user, support information on a combination of a binding molecule and a labeled molecule based on the calculated reactivity.

In addition, the information processing apparatus according to the present technique can further include an evaluating unit configured to estimate a significance of a binding molecule and/or a labeled molecule with respect to a target molecule based on image information.

In the present technique, the first signal group and the second signal group can be detection amounts having been standardized using at least one selected from excitation power density, exposure time, and detection device sensitivity.

In the present technique, next, a biological specimen analysis method is provided which includes the steps of:

acquiring a signal derived from a sample including a biological specimen;

calculating, based on the signal, when using a plurality of different binding molecules labeled by different labeled molecules, reactivity between a target molecule and each of the plurality of different binding molecules; and outputting the reactivity, wherein the signal includes a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule.

In addition, in the present technique, a biological specimen detection apparatus is provided which includes:

a signal acquiring unit configured to acquire a signal derived from a sample including a biological specimen;

a processing unit configured to calculate, based on the signal, when using a plurality of different binding molecules labeled by different labeled molecules, reactivity between a target molecule and each of the plurality of different binding molecules;

an output unit configured to output the reactivity; and a detecting unit configured to detect a signal emitted from a target molecule labeled using a binding molecule which is selected based on the output reactivity and which is labeled by a labeled molecule, wherein the signal includes a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule.

The biological specimen detection apparatus according to the present technique can further include a labeling unit configured to label a target molecule using a binding molecule which is selected based on the output reactivity and which is labeled by a labeled molecule.

The biological specimen detection apparatus according to the present technique can further include an analyzing unit configured to analyze the sample based on a signal detected by the detecting unit.

Furthermore, in the present technique, a biological specimen detection system is provided which includes:

an information processing apparatus including:

a signal acquiring unit configured to acquire a signal derived from a sample including a biological specimen;

a processing unit configured to calculate, based on the signal, when using a plurality of different binding molecules labeled by different labeled molecules, reactivity between a target molecule and each of the plurality of different binding molecules;

an output unit configured to output the reactivity, the signal including:

a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule, and a detection apparatus configured to detect a signal emitted from a target molecule labeled using a binding molecule which is selected based on the output reactivity and which is labeled by a labeled molecule.

BRIEF DESCRIPTION OF DRAWINGS

FIG. 14 is a photograph being a substitute for a diagram showing an image of each fluorescently-labeled antibody in a multi-stained image and an image of each fluorescent label in an unstained sample as a negative control in a second experimental example.

Figure 15:
Figure 15:

FIG. 15 is a photograph being a substitute for a diagram showing an image of each fluorescently-labeled antibody in a multi-stained image and an image of each fluorescent label in an unstained sample as a negative control in the second experimental example.

Figure 16:
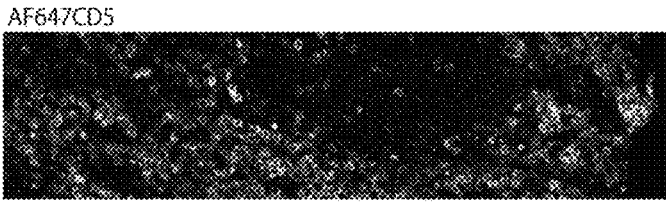
Figure 16:
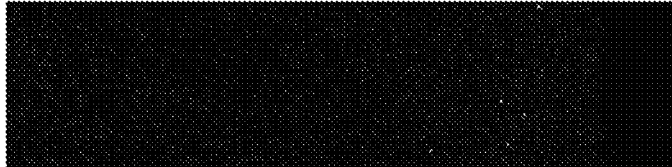

FIG. 16 is a photograph being a substitute for a diagram showing an image of each fluorescently-labeled antibody in a multi-stained image and an image of each fluorescent label in an unstained sample as a negative control in the second experimental example.

DESCRIPTION OF EMBODIMENTS

Hereinafter, a preferable embodiment for implementing the present technique will be described with reference to the drawings. The embodiment described below shows an example of a representative embodiment of the present technique, but the scope of the present technique should not be narrowly understood based on the embodiment. Descriptions will be given in the following order.

1. Information processing apparatus 1
(1) Target molecule
(2) Binding molecule
(3) Labeled molecule
(4) Signal acquiring unit 11
(5) Processing unit 12
(a) First signal group
(b) Second signal group
(c) Calculation of reactivity: processing unit 12
(d) Third signal
(e) Selection of combination of labeled molecule and binding molecule: processing unit 12
(6) Evaluating unit 13
(7) Output unit 14
(8) Presenting unit 15
(9) Storage Unit 16
(10) Display Unit 17
(11) User interface 18
2. Information processing system 2
3. Biological specimen detection apparatus 3, biological specimen detection system 4
(1) Detecting unit 31, detection apparatus 41
(2) Labeling unit 32, labeling apparatus 42
(3) Analyzing unit 33, analysis apparatus 43
4. Computer program
5. Biological specimen analysis method
6. Application examples
[Microscopic System 5000]
[Biological Specimen Analysis Apparatus 6100]

1. Information Processing Apparatus 1

Figure 1:
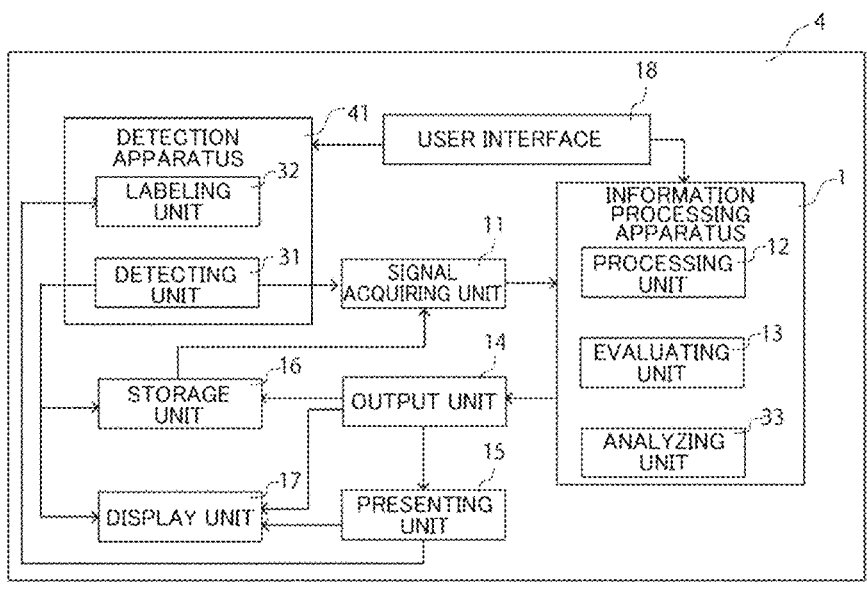
FIG. 1 is a block diagram showing a configuration example of a biological specimen detection system 4 according to the present technique.

FIG. 1 is a block diagram showing a configuration example of a biological specimen detection system 4 according to the present technique. An information processing apparatus 1 according to the present technique is an information processing apparatus that can be used in the biological specimen detection system 4 according to the present technique to be described later. The information processing apparatus 1 according to the present technique includes at least a processing unit 12. In addition, when necessary, the information processing apparatus 1 can also include a signal acquiring unit 11, an evaluating unit 13, an output unit 14, a presenting unit 15, a storage unit 16, a display unit 17, and a user interface 18. Hereinafter, respective units and the like will be described in detail.

(1) Target Molecule

In the present technique, a target molecule refers to a molecule that can be detected and/or analyzed by being bound with a binding molecule that is labeled by a labeled molecule to be described later and the target molecule can be selected by a person of ordinary skill in the art. Examples of a target molecule include molecules that can be detected and/or analyzed by being bound with a binding molecule that is labeled by a labeled molecule in analyses such as flow cytometry, microscopic observation, western blot, various arrays, and ELISA. In other words, the present technique can be used to support selection of a labeled molecule and a binding molecule to be used in such analyses.

More specifically, for example, a target molecule is a molecule which may be present in a living organism including bodily fluids such as blood and urine and tissue and of which examples include a biomolecule, a drug molecule, and a toxic molecule. Examples of a biomolecule include nucleic acids, proteins, sugars, lipids, and vitamins. Examples of a nucleic acid include DNA and RNA. Examples of proteins include an antigenic protein, an enzyme protein, a structural protein, and an adhesion protein.

Furthermore, target molecules include those which correlate to a change in a disease or a response to treatment as a biomarker and which act as an index.

(2) Binding Molecule

In the present technique, a binding molecule refers to a molecule which enables the target molecule described earlier to be detected and/or analyzed by binding with the target molecule and which can be selected by a person of ordinary skill in the art. Examples of the binding molecule include molecules which enable the target molecule to be detected and/or analyzed by binding with the target molecule in the various analyses described earlier.

More specifically, the binding molecule is a molecule that specifically binds with the target molecule and examples thereof include a biomolecule, a drug molecule, a high-molecular compound, and a low-molecular compound. Examples of the binding molecule include nucleic acids, artificial nucleic acids, proteins, peptides, sugars, lipids, and vitamins. Other examples of the binding molecule include DNA, RNA, PNA, and LNA. In addition, examples of an antibody-like molecule include an antigen cell surface marker, an enzyme protein, a structural protein and an adhesion protein.

A method of analyzing a target molecule using, as a binding molecule, an antibody to which a fluorochrome is bound as a labeled molecule to be described later is referred to as fluorescent immunostaining. Examples of fluorescent immunostaining include immunocytochemistry (ICC) and immunohistochemistry (IHC). ICC is a method of staining a cell separated from tissue or a cultured cell. IHC is a method of staining a target molecule in a section of tissue.

In addition, the fluorescent immunostaining includes direct fluorescent immunostaining and indirect fluorescent immunostaining. Direct fluorescent immunostaining is a method in which a target molecule is analyzed by having an antibody bound with a fluorochrome directly bind with the target molecule and detecting the fluorochrome. In indirect fluorescent immunostaining, an antibody (also referred to as a secondary antibody) bound with a fluorochrome binds with an antibody (also referred to as a primary antibody) that specifically binds with a target molecule and the secondary antibody further binds with the target molecule. In other words, indirect fluorescent immunostaining is a method of analyzing a target molecule by having an antibody (also referred to as a secondary antibody) bound with a fluorochrome bind with the target molecule via a primary antibody and detecting the fluorochrome.

The present technique can be suitably used to select a binding molecule and a labeled molecule to be used in fluorescent immunostaining.

(3) Labeled Molecule

In the present technique, a labeled molecule refers to a molecule that labels the binding molecule described earlier, and a target molecule can be detected and/or analyzed by having the binding molecule bind with the target molecule. Examples of a labeled molecule include molecules that can be used as a labeled molecule in the various analyses described earlier.

More specifically, an example of the labeled molecule is a dye. Examples of a dye include, but are not limited to, various fluorochromes having fluorescent wavelengths in a visible light range such as a fluorochrome in the Alexa Fluor (registered trademark) series, a fluorochrome in the DyLight (registered trademark) series, a fluorochrome in the BD Horizon Brilliant (registered trademark) series, and fluorochromes such as Atto, FITC, Cy3, Cy5, Cy5.5, Cy7, Rhodamine, PE (phycoerythrin), APC (Allophycocyanin), and PerCP.

In addition, in the present technique, a labeled molecule may be a molecule that is expressed as a part of a target molecule or a binding molecule such as a fluorescent protein included in a fluorescence fusion protein. Examples of a fluorescent protein include GFP, BFP, CFP, EGFP, EYFP, and PA-GFP.

(4) Signal Acquiring Unit 11

The signal acquiring unit 11 acquires a signal derived from a sample including a biological specimen. For example, a signal detected by a detection apparatus 41 that is a flow cytometer, a microscope, one of various photodetectors, or the like is acquired by the signal acquiring unit 11.

The signal acquiring unit 11 can not only acquire signals detected by various detection apparatuses 41 but can also acquire signal data inside a database stored in the storage unit 16 to be described later. For example, past detected data, data detected by other detection devices and accumulated in the database, and the like can be acquired by the signal acquiring unit 11.

(5) Processing Unit 12

Based on the signal acquired by the signal acquiring unit 11, the processing unit 12 calculates, when using a plurality of different binding molecules labeled by different labeled molecules, reactivity between a target molecule and each of the plurality of different binding molecules.

In the present technique, the signal may be a fluorescence signal itself, a specific signal/background, a specific signal/non-specific signal, or the like. In addition, the fluorescence signal may be in pixel units such as a signal/pixel or in cell units such as a fluorescence signal average/cell or a fluorescence signal sum/cell.

The signal to be a basis for calculations performed by the processing unit 12 includes a first signal group and a second signal group. The signal can also include a third signal. Hereinafter, each signal group and a method of calculating the reactivity that is carried out by the processing unit 12 will be described in detail.

(a) First Signal Group

The first signal group is a signal group that is acquired when each of a plurality of different binding molecules having been labeled by a labeled molecule of a same type is reacted with a target molecule. For example, each of a plurality of binding molecules C1 to C5 labeled with a labeled molecule F1 (F1-C1, F1-C2, F1-C3, F1-C4, and F1-C5) is reacted with the target molecule and a signal thereof is obtained.

Acquiring the first signal group enables a reactivity of the binding molecules C1 to C5 with respect to the target molecule to be evaluated. In other words, reactivities of different binding molecules C1 to C5 with respect to the target molecule can be compared with each other and the reactivities can be calculated. While an index representing reactivity is not particularly limited as long as reactivity can be evaluated, examples include fluorescence intensity, the number of binding molecules, absorbance, light scattering, phosphorescence, fluorescence lifetime, and mass.

While a method of calculating the number of binding molecules is not particularly limited and a general calculation method can be used, for example, the number of binding molecules may be calculated using an antibody count conversion method described in WO2020/022038.

Figure 2:
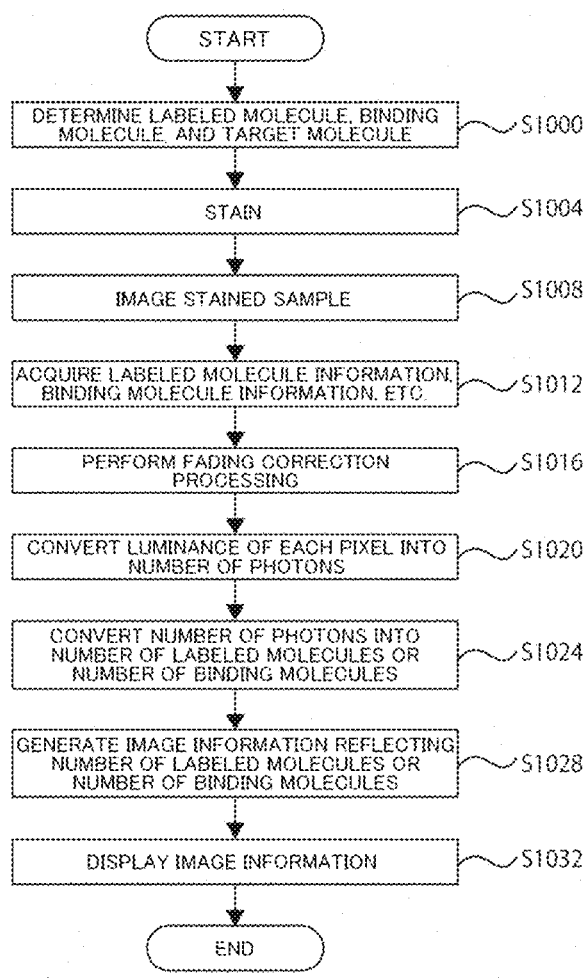
FIG. 2 is a flowchart showing an example of a method of calculating the number of binding molecules.

An example of a method of calculating the number of binding molecules will be described with reference to FIG. 2. In step S1000, a user determines a labeled molecule, a binding molecule, and a target molecule to be used in an analysis. In step S1004, the user creates a stained sample by staining the target molecule using the labeled molecule and the binding molecule.

In step S1008, the signal acquiring unit 11 of the information processing apparatus 1 images the stained sample to acquire captured image information. In step S1012, based on reagent identification information attached to the labeled molecule and the binding molecule used to generate the stained sample, the signal acquiring unit 11 acquires reagent information such as a fading coefficient, an absorption cross section, a quantum yield, and a fluorescent labeling ratio from the database in the storage unit 16. In addition, the signal acquiring unit 11 acquires excitation power density having been measured separately.

In step S1016, the processing unit 12 corrects a luminance of each pixel in the captured image information using the fading coefficient, the absorption cross section, the excitation power density, and the like (performs fading correction processing). In step S1020, the processing unit 12 converts the corrected luminance of each pixel into the number of photons. In step S1024, the processing unit 12 converts the number of photons into the number of labeled molecules or the number of binding molecules bound with the labeled molecules.

In step S1028, the processing unit 12 generates image information that reflects the number of labeled molecules or the number of binding molecules bound with the labeled molecules. In step S1032, the display unit 17 displays the image information on a display and the series of processing is ended.

In addition, while a method of calculating fluorescence intensity is also not particularly limited and a general calculation method can be used, for example, fluorescence intensity can be calculated using one or more numerical values selected from an excitation efficiency, a quantum yield, an absorption efficiency, and a ratio of fluorescence labeling (F/P value).

(b) Second Signal Group

The second signal group are signals acquired when each of binding molecules of a same type having been labeled by different labeled molecules is reacted with a target molecule. For example, each of binding molecules C1 of the same type having been labeled with different labeled molecules F1 to F5 (F1-C1, F2-C1, F3-C1, F4-C1, and F5-C1) is reacted with the target molecule and a signal thereof is obtained.

Acquiring the second signal group enables a difference in reactivities of the binding molecules with respect to the target molecule due to a difference in types of labeled molecules that label the binding molecule to be evaluated. In other words, reactivities between binding molecules labeled by different labeled molecules F1 to F5 and a target molecule can be compared with each other and evaluated. While an index representing reactivity is not particularly limited as long as reactivity can be evaluated in a similar manner to the first signal group, examples of such an index include the number of binding molecules and fluorescence intensity.

Since a method of calculating the number of binding molecules and a method of calculating fluorescence intensity are also similar to the methods described earlier with respect to the first signal group, a description thereof will be omitted here.

(c) Calculation of Reactivity: Processing Unit 12

In the present technique, based on the first signal group and the second signal group described earlier, when using a plurality of different binding molecules C2 to C5 labeled by different labeled molecules F2 to F5, reactivity between a target molecule and each of the plurality of different binding molecules C2 to C5 is calculated.

Specifically, since the reactivities of the binding molecules C1 to C5 labeled by the labeled molecule F1 with respect to the target molecule can be evaluated using the first signal group, for example, an index (for example, the number of binding molecules or fluorescence intensity) representing the reactivities of the binding molecules C1 to C5 with respect to the target molecule can be displayed in a column of the labeled molecule F1 in Table 1 below (refer to F1-C1, F1-C2, F1-C3, and F1-C4 in Table 1).

In addition, since a difference in reactivities of the binding molecule C1 with respect to the target molecule due to a difference in types of the labeled molecules F1 to F5 that label the binding molecule C1 can be evaluated using the second signal group, for example, an index (for example, the number of binding molecules or fluorescence intensity) representing the reactivities of the binding molecule C1 labeled with the labeled molecules F1 to F5 with respect to the target molecule can be displayed in a row of the binding molecule C1 in Table 1 below (refer to F1-C1, F2-C1, F3-C1, F4-C1, and F5-C1 in Table 1).

Furthermore, based on the first signal group and the second signal group, when using the plurality of different binding molecules C2 to C5 labeled by the different labeled molecules F2 to F5, reactivity between the target molecule and each of the plurality of different binding molecules C2 to C5 is calculated. Specifically, for example, a coefficient of a difference in reactivities between the binding molecules C1 and C2 with respect to the target molecule is estimated based on the reactivity of the binding molecule C1 labeled by the labeled molecule F1 with respect to the target molecule and the reactivity of the binding molecule C2 labeled by the labeled molecule F1 with respect to the target molecule, a coefficient of a difference in reactivities of the target molecule and the binding molecule C1 between a case where the binding molecule C1 is labeled by the labeled molecule F1 and a case where the binding molecule C1 is labeled by the labeled molecule F2 is estimated based on the reactivity of the binding molecule C1 labeled by the labeled molecule F1 with respect to the target molecule and the reactivity of the binding molecule C1 labeled by the labeled molecule F2 with respect to the target molecule, and by applying these coefficients, the reactivity of the binding molecule C2 labeled by the labeled molecule F2 with respect to the target molecule can be calculated.

Using similar methods, by calculating reactivities with respect to the empty fields in Table 1 below, a matrix can be created with respect to each reactivity when using a plurality of different binding molecules C1 to C5 labeled by different labeled molecules F1 to F5.

TABLE 1

| [REACTIVITY OF BINDING MOLECULES] | | | | | | |
|---|---|---|---|---|---|---|
| | | LABELED MOLECULE | | | | |
| | | F1 | F2 | F3 | F4 | F5 |
| BINDING | C1 | F1-C1 | F2-C1 | F3-C1 | F4-C1 | F5-C1 |
| MOLECULE | C2 | F1-C2 | | | | |
| | C3 | F1-C3 | | | | |
| | C4 | F1-C4 | | | | |
| | C5 | F1-C5 | | | | |

The index of reactivity of the first signal group and the index of reactivity of the second signal group may differ from each other. For example, a specific example of a method of calculating an index of reactivity between a target molecule and a binding molecule in a combination of a labeled molecule and a binding molecule that is not actually measured when using the number of binding molecules for the first signal group and using fluorescence intensity for the second signal group will be described below.

Numbers of binding molecules calculated based on captured images or the like acquired when reacting a plurality of different binding molecules C1 to C3 labeled by the same labeled molecule F1 with a target molecule as the first signal group F1-C1, F1-C2, and F1-C3 are shown in Table 2 below.

TABLE 2

| [NUMBER OF BINDING MOLECULES] | | | | | |
|---|---|---|---|---|---|
| | | LABELED MOLECULE | | | |
| | | F1 | F2 | F3 | F4 |
| BINDING | C1 | F1-C1 | | | |
| MOLECULE | C2 | F1-C2 | | | |
| | C3 | F1-C3 | | | |

Fluorescence intensities calculated based on captured images or the like acquired when reacting binding molecules C1 of the same type labeled by different labeled molecules F1 to F4 with a target molecule as the second signal group F1-C1, F2-C1, F3-C1, and F4-C1 are shown in Table 3 below. In doing so, a signal/background ratio of fluorescence intensity can also be used as will be described later.

TABLE 3

| [FLUORESCENCE INTENSITY] | | | | | |
|---|---|---|---|---|---|
| | | LABELED MOLECULE | | | |
| | | F1 | F2 | F3 | F4 |
| BINDING | C1 | F1-C1 | F2-C1 | F3-C1 | F4-C1 |
| MOLECULE | C2 | | | | |
| | C3 | | | | |

In this case, for example, when using fluorescence intensity as an index of reactivity, although fluorescence intensity of the labeled molecule F4 and the binding molecule C3 is not actually measured, the fluorescence intensity can be calculated according to the following expression.

Reactivity index (fluorescence intensity) of F4–C3= (number of binding molecules of F1–C3/number of binding molecules of F1–C1)×(fluorescence intensity of F4–C1)

Using similar methods, by calculating an index of reactivities with respect to the empty fields in Table 3 described above, a matrix can be created with respect to each fluorescence intensity when using a plurality of different binding molecules C1 to C3 labeled by different labeled molecules F1 to F4.

By referring to a matrix created in this manner, when selecting a binding molecule and a labeled molecule to be used when detecting and/or analyzing a target molecule, an optimal combination of a binding molecule and a labeled molecule can be selected. As a result, accuracy of detection and/or analysis of a target molecule can be improved.

As described above, in the present technique, since each reactivity among the types of the labeled molecules F2 to F5 and the types of the binding molecules C2 to C5 which have not been actually measured can be calculated based on the first signal group and the second signal group, there is no need to actually measure all combinations of the binding molecules and the labeled molecules. In other words, in the present technique, each reactivity among the types of the labeled molecules and the types of the binding molecules can be calculated from a small number of pieces of actually measured data. In other words, the processing unit 12 can calculate a reactivity with the target molecule with respect to combinations of the labeled molecules and the binding molecules which have not been actually measured.

In addition, using the present technique enables the user to avoid the trouble of having to select a binding molecule and a labeled molecule to be used when detecting and/or analyzing a target molecule and prevents accuracy of detection and/or analysis of the target molecule from varying according to the user's experience.

(d) Third Signal

The third signal is a signal that is acquired when using negative control. Examples of a signal acquired when using negative control include a signal acquired when reacting an unlabeled binding molecule, a signal acquired from an unstained sample not using a binding molecule, and a signal acquired when using an isotype control antibody.

A background in each detection channel can be calculated based on the third signal. Specifically, as the background in each detection channel, leakage of an autofluorescence signal, leakage of a signal derived from other labeled molecules such as other fluorochrome signals and the like can be calculated.

In the calculation of a background in each detection channel, leakage from labeled molecules in channels other than a given channel is preferably taken into consideration. As the leakage from labeled molecules in other channels, for example, a sum of leakages in respective labeled molecules calculated from the second signal group (a signal group acquired when each of binding molecules of a same type having been labeled by labeled molecules of different types is reacted) can be used. In addition, for example, a leakage to the given channel when using a binding molecule labeled by all labeled molecules in channels other than the given channel may be calculated.

The first signal group, the second signal group, and the third signal can use a detection amount normalized using at least one selected from excitation power density, exposure time, and detecting device sensitivity. For example, when a common device is used or when inter-device correction can be performed by management prior to shipment, an error due to degradation over time or usage environment can be calibrated between devices or inside a device during daily maintenance. However, even when using different devices or when inter-device or intra-device calibration cannot be performed prior to shipment or during daily maintenance, by performing normalization using at least one selected from excitation power density, exposure time, and detecting device sensitivity, a measurement condition can be satisfied.

In addition, as will be described later, by accumulating data of the first signal group, the second signal group, the third signal, background, and the like and making a database, accuracy of inter-device correction can be further improved in accordance with a trend (correction coefficient) of inter-device error.

In the present technique, as described earlier, while fluorescence intensity can be used as an index representing reactivity, a signal/background ratio of fluorescence intensity is preferably used as an index. Since noise can be removed by using a signal/background ratio of fluorescence intensity as an index representing reactivity, detection and/or analysis with higher accuracy can be performed.

(e) Selection of Combination of Labeled Molecule and Binding Molecule: Processing Unit 12

In the present technique, a combination of a labeled molecule and a binding molecule which are preferable with respect to a target molecule can be selected based on a calculated reactivity between the target molecule and the binding molecule.

For example, when using a signal/background ratio of fluorescence intensity as an index representing reactivity, a combination of a labeled molecule and a binding molecule causing the signal/background ratio of fluorescence intensity to equal or exceed a threshold can be selected. Accordingly, all labeled binding molecules can be detected. In addition, a combination of a labeled molecule and a binding molecule which maximizes a sum of signal/background ratios of fluorescence intensity can be selected. Accordingly, since the signal/background ratio increases, detection becomes easier. Furthermore, a combination of a labeled molecule and a binding molecule can be selected by combining the above.

Moreover, for example, a combination of a labeled molecule and a binding molecule which maximizes a sum of differences between a signal of fluorescence intensity and a background of fluorescence intensity can also be selected. Accordingly, since a signal higher than a background can be obtained, detection becomes easier.

In addition, a combination of a labeled molecule and a binding molecule can be selected based on a magnitude of a signal of fluorescence intensity. Accordingly, since autofluorescence of a sample to become a background tends to exhibit high luminance on a short wavelength side, all signal/background ratios can be increased.

Furthermore, a combination of a labeled molecule and a binding molecule can also be selected so that labels are to be assigned in a descending order of a signal of the fluorescence intensity to binding molecules in an ascending order of a value of the first signal group. Accordingly, a condition which is advantageous to sequentially detecting binding molecules that are difficult to detect can be set and combinations equal to or lower than a detection limit can be eliminated.

Moreover, a combination of a labeled molecule and a binding molecule can be selected so that labels are to be assigned in an ascending order of a length of a detection wavelength to binding molecules in a descending order of a value of the first signal group. At this point, when there are a plurality of candidates, a combination that provides a larger index calculation value can be selected.

(6) Evaluating Unit 13

The information processing apparatus 1 according to the present technique can further include the evaluating unit 13 which estimates a significance of a binding molecule and/or a labeled molecule with respect to a target molecule based on image information. Specifically, in the evaluating unit 13, a significance of a binding molecule and/or a labeled molecule with respect to a target molecule is estimated such as determining whether or not to raise luminance in accordance with a type of the binding molecule or the labeled molecule, considering how a threshold is to be set, and lowering a background to enable an object signal to be picked up more readily when the signal is weak.

(7) Output Unit 14

The information processing apparatus 1 according to the present technique can include the output unit 14 which outputs various types of information. In addition to information processed by the processing unit 12 described earlier and various information related to the calculation of reactivity including various signals and various thresholds, the output unit 14 can output all data including various kinds of information related to detection performed in order to calculate reactivity.

Specifically, the output unit 14 can output a matrix of combinations of a binding molecule and a labeled molecule calculated as described above or a combination of a binding molecule and a labeled molecule selected as described above. In addition, the output unit 14 can also output a significance of a binding molecule and/or a labeled molecule with respect to a target molecule as estimated by the evaluating unit 13.

(8) Presenting Unit 15

The presenting unit 15 presents the user with, based on the output reactivity, support information on a combination of a binding molecule and a labeled molecule. Conventionally, since the selection of a combination of a labeled molecule and a binding molecule with respect to a target molecule has been performed by the user, there are cases where the combination is not appropriate and, even if the user has a lot of experience, the selection is an extremely time-consuming task. However, according to the present technique, since a labeled molecule and a binding molecule of an optimum combination is presented in accordance with, for example, a type of a target molecule, a state of a sample, or the like to be an object of detection or analysis based on the reactivity having been calculated by the processing unit 12 and output by the output unit 14, detection with high accuracy can be performed regardless of the experience of the user.

In the present technique, the presenting unit 15 is not essential and a labeling device or the like can automatically label a target molecule without involving the user. For example, a combination of a binding molecule and a labeled molecule output by the output unit 14 can be directly output to various labeling devices and, based on the combination of the binding molecule and the labeled molecule acquired by the various labeling devices, the various labeling devices can also automatically label a target molecule using a combination of a binding molecule and a labeled molecule that is optimal to the target molecule.

(9) Storage Unit 16

The information processing apparatus 1 according to the present technique can include the storage unit 16 in which various types of information are stored. The storage unit 16 can accumulate and store all kinds of data including various information related to the calculation of reactivity including information processed by the processing unit 12, various signals and various thresholds, and various information related to detection performed in order to calculate reactivity.

The storage unit 16 is not essential to the information processing apparatus 1 according to the present technique and each piece of information can be output from the output unit 14 to the outside of the apparatus and stored in an external storage apparatus 21 such as that described later. The storage apparatus 21 can be provided in a cloud environment and connected to the information processing apparatus 1 according to the present technique via a network. In this case, various kinds of information stored in the storage apparatus 21 on the cloud can also be shared among a plurality of users.

Figure 7:
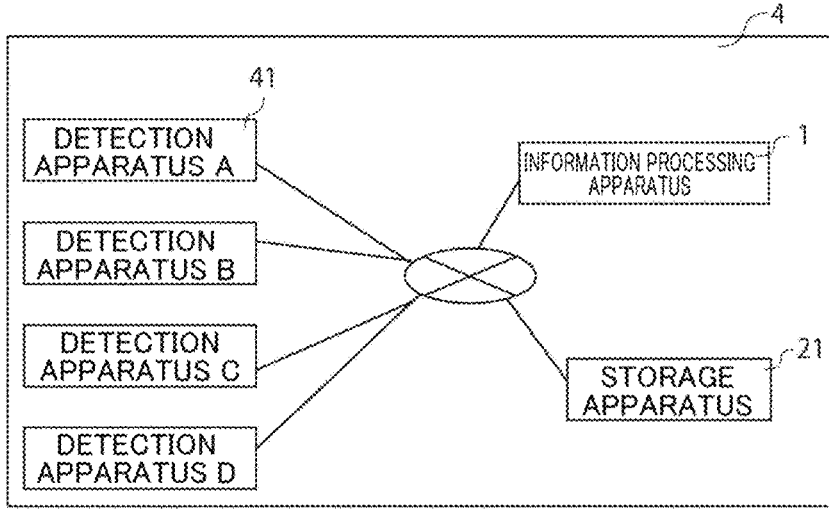
FIG. 7 is a conceptual diagram showing an example of the biological specimen detection system 4 according to the present technique which differs from the examples shown in FIGS. 5 and 6.

A database can be constructed in the storage unit 16 or the external storage apparatus 21 based on information output by the output unit 14, detection data detected by external detection apparatuses 41A to 41D and the like as shown in FIG. 7 to be described later, detection data collected from other samples, and the like. In this case, the processing unit 12 can perform various kinds of processing by referring to the database. Specifically, the processing unit 12 can refer to the database accumulating the first signal group, the second signal group, the third signal, backgrounds, and various kinds of calculated data. For example, by referring to past performance data, detection data detected by the external detection apparatuses 41A to 41D, detection data collected from other samples, and the like, even if the user himself/ herself does not actually perform a measurement, reactivity between a target molecule and a binding molecule among each type of labeled molecules and each type of binding molecules can be calculated and a matrix of combinations of a binding molecule and a labeled molecule can also be created.

In addition, by calculating a correction coefficient using various signals aggregated in a database, accuracy of the correction coefficient can also be improved as the number of pieces of data increases.

Furthermore, by referring to a database accumulating a matrix of combinations of a binding molecule and a labeled molecule and verifying a result of a detection and/or an analysis of a target molecule using a combination of a binding molecule and a labeled molecule, a recommendation accuracy of a recommended combination can also be improved.

(10) Display Unit 17

The information processing apparatus 1 according to the present technique can include the display unit 17 that displays various types of information output by the output unit 14. As the display unit 17, for example, a general display apparatus such as a display or a printer can be used.

(11) User interface 18

The information processing apparatus 1 according to the present technique can further include the user interface 18 to be operated by the user. Through the user interface 18, the user can access and control each unit.

In the present technique, the user interface 18 is not essential and an external operation apparatus may be connected. As the user interface 18, for example, a mouse or a keyboard can be used.

2. Information Processing System 2

Figure 3:
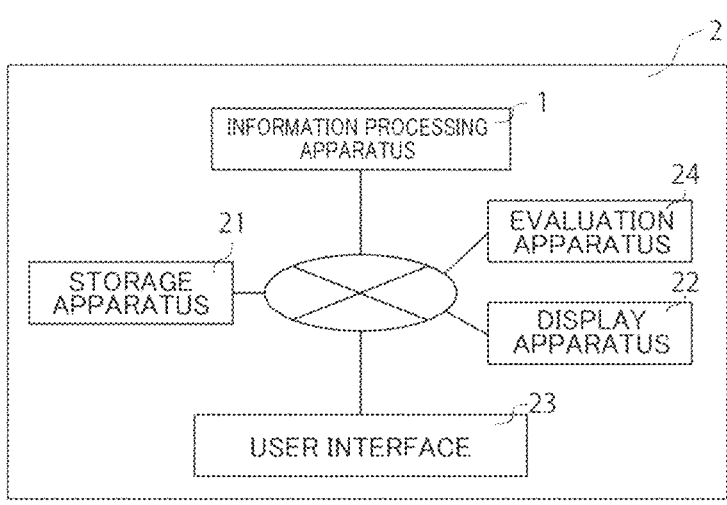
FIG. 3 is a conceptual diagram showing an example of an information processing system 2 according to the present technique.

FIG. 3 is a conceptual diagram showing an example of an information processing system 2 according to the present technique. The information processing system 2 according to the present technique includes the information processing apparatus 1 according to the present technique described earlier and the storage apparatus 21 that stores information calculated by the information processing apparatus 1. In addition, the information processing system 2 according to the present technique can include, as necessary, an evaluation apparatus 24, a display apparatus 22, and a user interface 23. Since details of the information processing apparatus 1 are the same as details of the information processing apparatus 1 according to the present technique described earlier, descriptions thereof will be omitted here. In addition, since details of the evaluation apparatus 24, the storage apparatus 21, the display apparatus 22, and the user interface 23 are also the same as details of the evaluating unit 13, the storage unit 16, the display unit 17, and the user interface 18 of the information processing apparatus 1 according to the present technique described earlier, descriptions thereof will be omitted here.

3. Biological Specimen Detection Apparatus 3, Biological Specimen Detection System 4

Figure 4:
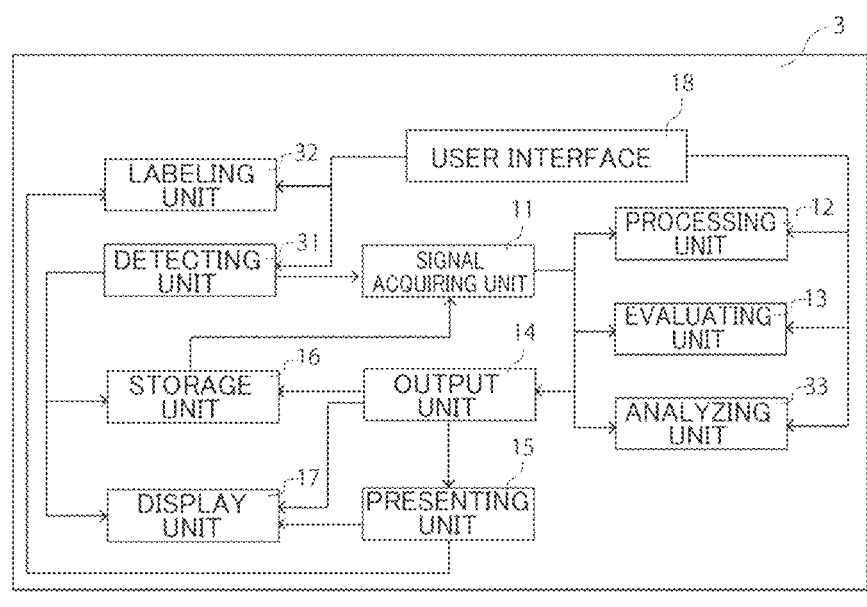
FIG. 4 is a block diagram showing an example of a biological specimen detection apparatus 3 according to the present technique.

FIG. 4 is a block diagram showing an example of the biological specimen detection apparatus 3 according to the present technique. The biological specimen detection apparatus 3 according to the present technique includes a detecting unit 31, the signal acquiring unit 11, the processing unit 12, and the output unit 14. In addition, the biological specimen detection apparatus 3 according to the present technique can also include, as necessary, a labeling unit 32, the evaluating unit 13, the presenting unit 15, the storage unit 16, the display unit 17, the user interface 18, an analyzing unit 33, and the like. Since details of the signal acquiring unit 11, the processing unit 12, the output unit 14, the evaluating unit 13, the presenting unit 15, the storage unit 16, the display unit 17, and the user interface 18 are the same as details of the signal acquiring unit 11, the processing unit 12, the output unit 14, the evaluating unit 13, the presenting unit 15, the storage unit 16, the display unit 17, and the user interface 18 of the information processing apparatus 1 according to the present technique described earlier, descriptions thereof will be omitted here.

Figure 5:
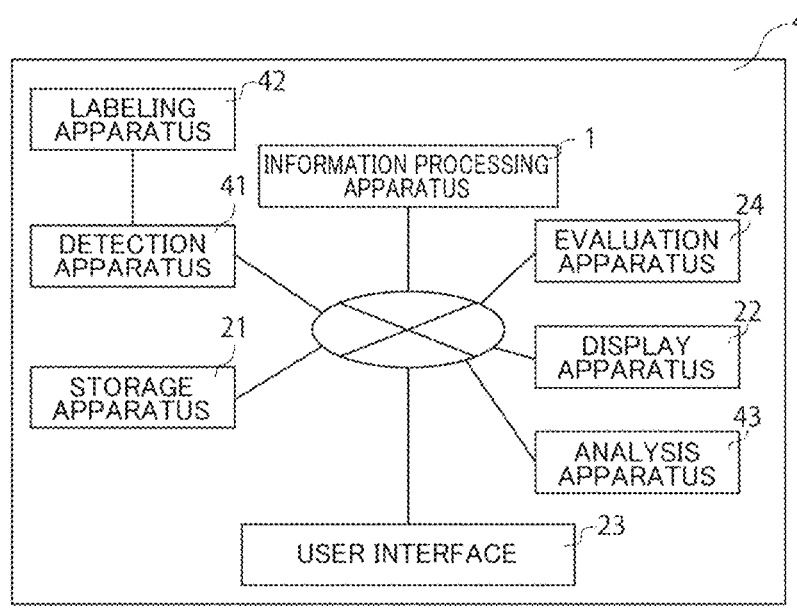
FIG. 5 is a conceptual diagram showing an example of the biological specimen detection system 4 according to the present technique.

FIG. 5 is a conceptual diagram showing an example of the biological specimen detection system 4 according to the present technique. The biological specimen detection system 4 according to the present technique includes the detection apparatus 41 and the information processing apparatus 1 according to the present technique described earlier. In addition, the biological specimen detection system 4 according to the present technique can also include, as necessary, the labeling unit 32 or a labeling apparatus 42, the evaluating unit 13 or the evaluation apparatus 24, the storage unit 16 or the storage apparatus 21, the display apparatus 22, the user interface 23, the analyzing unit 33 or an analysis apparatus 43, and the like. Since details of the information processing apparatus 1 are the same as details of the information processing apparatus 1 described earlier, descriptions thereof will be omitted here. Furthermore, since details of the evaluating unit 13 or the evaluation apparatus 24, the storage unit 16 or the storage apparatus 21, the display apparatus 22, and the user interface 23 are the same as details of the evaluating unit 13, the storage unit 16, the display unit 17, and the user interface 18 of the information processing apparatus 1 according to the present technique described earlier, descriptions thereof will be omitted here.

Figure 6:
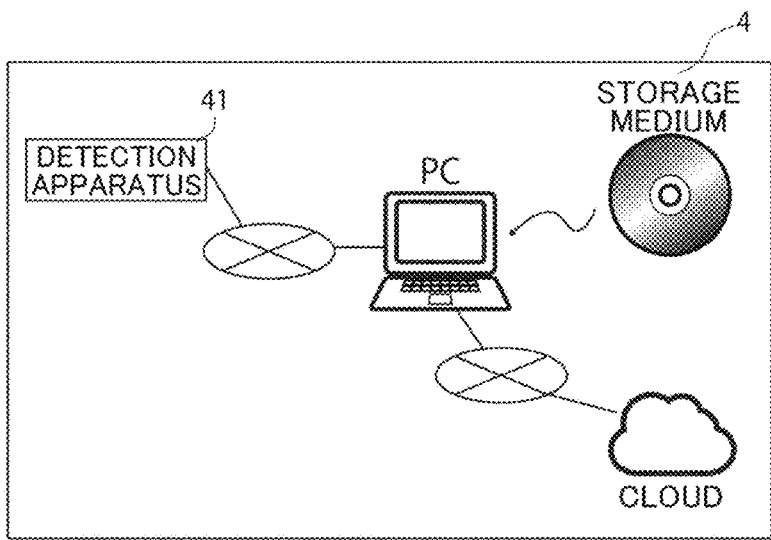
FIG. 6 is a conceptual diagram showing an example of the biological specimen detection system 4 according to the present technique which differs from the example shown in FIG. 5.

FIG. 6 is a conceptual diagram showing an example of the biological specimen detection system 4 according to the present technique that differs from FIG. 5. The biological specimen detection system 4 according to the present technique includes the detection apparatus 41 and a computer program to be described later.

(1) Detecting Unit 31, Detection Apparatus 41

The detecting unit 31 and the detection apparatus 41 detect a signal emitted from a target molecule labeled using a binding molecule having been labeled by a labeled molecule. A combination of a labeled molecule and a binding molecule for labeling the target molecule can be selected based on reactivity output from the output unit 14.

As the detecting unit 31 and the detection apparatus 41 that can be used in the present technique, a general detecting unit and a general detection apparatus can be freely used as long as a signal emitted from the binding molecule can be detected. For example, a detecting unit and a detection apparatus that can be used in analyses such as flow cytometry, microscopic observation, western blot, various arrays, and ELISA can be used.

In the biological specimen detection system 4 according to the present technique, the information processing apparatus 1 and/or the storage apparatus 21 can be provided in a cloud environment to be connected to the detection apparatus 41 via a network. In this case, various kinds of information stored in the storage apparatus 21 on the cloud can also be shared among a plurality of users. Specifically, for example, as shown in FIG. 7, a plurality of detection apparatuses 41A to 41D can be connected to the information processing apparatus 1 and/or the storage apparatus 21 via a network, the information processing apparatus 1 can perform processing using signals detected by the plurality of detection apparatuses 41A to 41D, and a matrix of reactivities in combinations of a labeled molecule and a binding molecule output from the information processing apparatus 1 can be shared among the plurality of detection apparatuses 41A to 41D.

(2) Labeling Unit 32, Labeling Apparatus 42

The labeling unit 32 and the labeling apparatus 42 label a target molecule inside a biological specimen using a binding molecule having been labeled by a labeled molecule. Based on the matrix of reactivities in combinations of a labeled molecule and a binding molecule output from the output unit 14, the labeling unit 32 and the labeling apparatus 42 can label the target molecule using an optimal combination of a labeled molecule and a binding molecule. As a result, it is possible to improve accuracy of target molecule detection.

The labeling unit 32 and the labeling apparatus 42 are not essential in the biological specimen detection apparatus 3 and the biological specimen detection system 4 according to the present technique and a target molecule can be labeled using an external labeling apparatus or the like based on the matrix of reactivities in combinations of a labeled molecule and a binding molecule output from the output unit 14.

(3) Analyzing Unit 33, Analysis Apparatus 43

The analyzing unit 33 and the analysis apparatus 43 analyze the sample based on a signal detected by the detecting unit 31 or the detection apparatus 41. More specifically, a type, an amount, characteristics, and the like of a target molecule included in the sample can be analyzed based on a signal detected by the detecting unit 31 or the detection apparatus 41.

The analyzing unit 33 and the analysis apparatus 43 are not essential in the biological specimen detection apparatus 3 and the biological specimen detection system 4 according to the present technique and characteristics and the like of a target molecule inside a sample can also be analyzed using an external analysis apparatus or the like based on a signal detected by the detecting unit 31 or the detection apparatus 41. For example, the analyzing unit 33 and the analysis apparatus 43 may be implemented in a personal computer or a CPU, or may be stored as a program in a hardware resource including a recording medium (for example, a nonvolatile memory (a USB memory), an HDD, or a CD) and the like, and can be caused to function by the personal computer or the CPU. In addition, the analyzing unit 33 and the analysis apparatus 43 can be connected via a network to each unit of the biological specimen detection apparatus 3 and the biological specimen detection system 4.

4. Computer Program

A computer program according to the present technique is a computer program causing a computer to realize: a signal acquisition function of acquiring a signal derived from a sample including a biological specimen; a processing function of calculating, based on the signal, when using a plurality of different binding molecules labeled by different labeled molecules, reactivity between a target molecule and each of the plurality of different binding molecules; and an output function of outputting the reactivity, wherein the signal includes the first signal group and the second signal group.

The computer program according to the present technique is recorded on an appropriate recording medium. In addition, the computer program according to the present technique can be stored in a cloud environment or the like and downloaded to a personal computer or the like via a network to be used by the user. Since the signal acquisition function, the processing function, and the output function in the computer program according to the present technique are the same as the respective functions carried out by the signal acquiring unit 11, the processing unit 12, and the output unit 14 of the information processing apparatus 1 described earlier, a description thereof will be omitted here.

5. Biological Specimen Analysis Method

Figure 8:
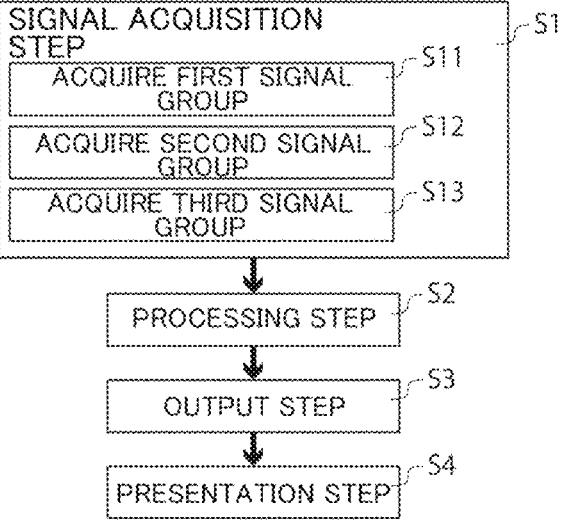
FIG. 8 is a flowchart showing an example of an information processing method according to the present technique.

FIG. 8 is a flowchart showing an example of the biological specimen analysis method according to the present technique. The biological specimen analysis method according to the present technique is a method of performing at least a signal acquisition step S1, a processing step S2, and an output step S3. In addition, when necessary, a presentation step S4 and, although not illustrated, an evaluation step, a storage step, a display step, and the like can also be performed. Since the signal acquisition step S1, the processing step S2, the output step S3, the presentation step S4, the evaluation step, the storage step, and the display step are the same as methods carried out by the signal acquiring unit 11, the processing unit 12, the output unit 14, the presenting unit 15, the evaluating unit 13, the storage unit 16, and the display unit 17 of the information processing apparatus 1 described earlier, a description thereof will be omitted here.

6. Application Examples

The present technique can be applied to, for example, a microscopic system 5000 and a biological specimen analysis apparatus 6100.

[Microscopic System 5000]

Figure 9:
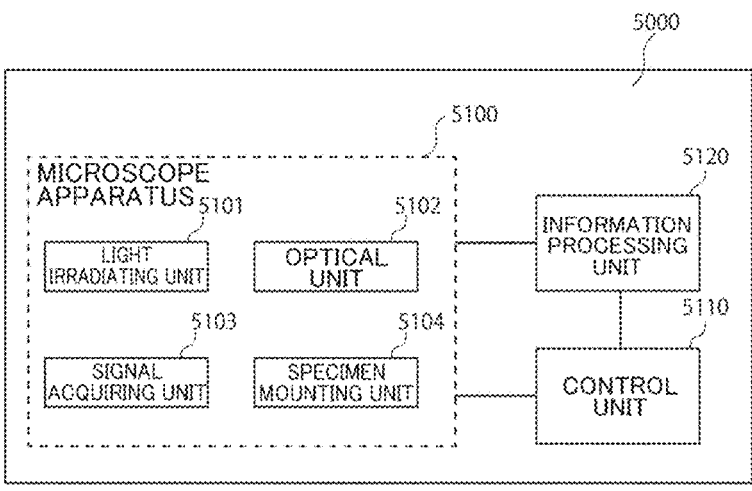
FIG. 9 is a diagram schematically showing an overall configuration of a microscopic system 5000.

FIG. 9 shows a configuration example of the microscopic system 5000 according to the present disclosure. The microscopic system 5000 shown in FIG. 9 includes a microscope apparatus 5100, a control unit 5110, and an information processing unit 5120. The microscope apparatus 5100 includes a light irradiating unit 5101, an optical unit 5102, and a signal acquiring unit 5103. The microscope apparatus 5100 may further include a specimen mounting unit 5104 on which a living organism-derived specimen S is arranged. Note that a configuration of the microscope apparatus 5100 is not limited to that shown in FIG. 9 and, for example, the light irradiating unit 5101 may be present outside of the microscope apparatus 5100 and a light source not included in the microscope apparatus 5100 may be used as the light irradiating unit 5101. In addition, the light irradiating unit 5101 may be arranged so that the specimen mounting unit 5104 becomes sandwiched between the light irradiating unit 5101 and the optical unit 5102 and may be arranged on, for example, a side where the optical unit 5102 is present. The microscope apparatus 5100 may be configured to be capable of executing one or two or more of bright-field observation, phase difference observation, differential interference observation, polarization observation, fluorescent observation, and dark-field observation.

The microscopic system 5000 may be configured as a so-called WSI (Whole Slide Imaging) system or a digital pathology imaging system and may be used for pathological diagnoses. In addition, the microscopic system 5000 may be configured as a fluorescent imaging system and, particularly, a multiplex fluorescent imaging system.

For example, the microscopic system 5000 may be used to perform an intraoperative pathological diagnosis or a remote pathological diagnosis. In intraoperative pathological diagnosis, while an operation is being performed, the microscope apparatus 5100 may acquire data of the living organism-derived specimen S acquired from a subject of the operation and transmit the data to the information processing unit 5120. In remote pathological diagnosis, the microscope apparatus 5100 may transmit the acquired data of the living organism-derived specimen S to the information processing unit 5120 present at a location that is separated from the microscope apparatus 5100 (another room, another building, or the like). In addition, in these diagnoses, the information processing unit 5120 receives and outputs the data. A user of the information processing unit 5120 may perform a pathological diagnosis based on the output data.

(Living Organism-Derived Specimen S)

The living organism-derived specimen S may be a specimen including a biogenic substance. The biogenic substance may be tissue or a cell of a living organism, a liquid component (blood, urine, or the like) of the living organism, a culture, or a living cell (a myocardial cell, a nerve cell, a fertilized egg, or the like).

The living organism-derived specimen S may be a solid object and may be a sample fixed by an immobilization reagent such as paraffin or a solid object formed by freezing. The living organism-derived specimen S may be a section of the solid object. A specific example of the living organism-derived specimen S is a section of a biopsy specimen.

The living organism-derived specimen S may be subjected to treatment such as staining or labeling. The treatment may be staining in order to indicate a form of a biogenic substance or to indicate a substance (such as a surface antigen) included in the biogenic substance and examples of the staining can include HE (Hematoxylin-Eosin) staining and Immunohistochemistry staining. The treatment described above may be performed on the living organism-derived specimen S using one or two or more reagents and the reagents may be a fluorochrome, a coloring reagent, a fluorescent protein, or a fluorescently-labeled antibody.

The sample may be fabricated from a tissue sample for the purpose of a pathological diagnosis, a clinical examination, or the like. In addition to being derived from a human body, the sample may be derived from an animal, a plant, or other materials. Characteristics of the sample vary depending on a type of tissue to be used (such as an organ or a cell), a type of an object disease, an attribute of a subject (e.g., age, sex, blood type, or race), or a lifestyle of the subject (e.g., a diet, an exercise habit, or a smoking habit). The samples may be managed by attaching identification information (a barcode, a QR code (registered trademark), or the like) that enable each sample to be identified.

(Light Irradiating Unit 5101)

The light irradiating unit 5101 is made up of a light source for illuminating the living organism-derived specimen S and an optical unit that guides light radiated from the light source to a sample. The light source may irradiate the living organism-derived specimen S with visible light, ultraviolet light, infrared light, or a combination thereof. The light source may be one or two or more of a halogen light source, a laser light source, an LED light source, a mercury light source, and a xenon light source. A type and/or a wavelength of a light source in fluorescent observation may be provided in plurality and may be appropriately selected by a person of ordinary skill in the art. The light irradiating unit 5101 may have a transmission type configuration, a reflection type configuration, or a vertical illumination type (a coaxial vertical illumination type or a side illumination type) configuration.

(Optical Unit 5102)

The optical unit 5102 is configured to guide light from the living organism-derived specimen S to the signal acquiring unit 5103. The optical unit 5102 may be configured to enable the microscope apparatus 5100 to observe or image the living organism-derived specimen S.

The optical unit 5102 may include an objective lens. A type of the objective lens may be appropriately selected by a person of ordinary skill in the art in accordance with an observation system. In addition, the optical unit 5102 may include a relay lens for relaying an image enlarged by the objective lens to the signal acquiring unit 5103. The optical unit 5102 may further include optical components other than the objective lens and the relay lens such as an eyepiece, a phase plate, and a condenser lens.

In addition, the optical unit 5102 may further include a wavelength separating unit configured to separate light with a predetermined wavelength from among light from the living organism-derived specimen S. The wavelength separating unit may be configured to selectively enable light with a predetermined wavelength or a predetermined wavelength range to reach the signal acquiring unit 5103. The wavelength separating unit may include one or two or more of a filter, a polarizing plate, a prism (a Wollaston prism), and a diffraction grating which selectively transmit light. Optical components included in the wavelength separating unit may be arranged on, for example, an optical path from the objective lens to the signal acquiring unit 5103. When fluorescent observation is to be performed and, particularly, when an excitation light irradiating unit is included, the wavelength separating unit is provided inside the microscope apparatus 5100. The wavelength separating unit may be configured to separate beams of fluorescent light from each other or to separate white light and fluorescent light from each other.

(Signal Acquiring Unit 5103)

The signal acquiring unit 5103 may be configured to be capable of receiving light from the living organism-derived specimen S and converting the light into an electric signal and, particularly, a digital electric signal. The signal acquiring unit 5103 may be configured to be capable of acquiring data related to the living organism-derived specimen S based on the electric signal. The signal acquiring unit 5103 may be configured to be capable of acquiring data of an image (particularly, a still image, a time-lapse image, or a moving image) of the living organism-derived specimen S and, particularly, capable of acquiring data of an image having been enlarged by the optical unit 5102. The signal acquiring unit 5103 includes one or a plurality of imaging elements such as CMOSs or CCDs including a plurality of pixels being aligned and arranged one-dimensionally or two-dimensionally. The signal acquiring unit 5103 may include imaging elements for acquiring low-resolution images and imaging elements for acquiring high-resolution images or include sensing imaging elements for AF or the like and image-outputting imaging elements for observation or the like. In addition to the plurality of pixels, the imaging elements may include a signal processing unit (including one or two or more of a CPU, a DSP, and a memory) that performs signal processing using a pixel signal from each pixel and an output control unit that controls output of image data generated from the pixel signal and processing data generated by the signal processing unit. The imaging element including the plurality of pixels, the signal processing unit, and the output control unit may preferably be configured as a 1-chip semiconductor device.

The microscopic system 5000 may further include an event detection sensor. The event detection sensor may be configured to include a pixel that photoelectrically converts incident light and to detect a change in brightness of the pixel exceeding a predetermined threshold as an event. The event detection sensor may particularly be an asynchronous sensor.

(Control Unit 5110)

The control unit 5110 controls imaging by the microscope apparatus 5100. For the purpose of imaging control, the control unit 5110 may adjust a positional relationship between the optical unit 5102 and the specimen mounting unit 5104 by driving movement of the optical unit 5102 and/or the specimen mounting unit 5104. The control unit 5110 may move the optical unit 5102 and/or the specimen mounting unit 5104 in a direction where the units approach each other or separate from each other (for example, in an optical axis direction of the objective lens). In addition, the control unit 5110 may move the optical unit 5102 and/or the specimen mounting unit 5104 in any direction on a plane perpendicular to the optical axis direction. The control unit 5110 may control the light irradiating unit 5101 and/or the signal acquiring unit 5103 for the purpose of imaging control.

(Specimen Mounting Unit 5104)

The specimen mounting unit 5104 may be configured so that a position of the living organism-derived specimen S on the specimen mounting unit 5104 can be fixed and may be a so-called stage. The specimen mounting unit 5104 may be configured to be capable of moving the position of the living organism-derived specimen S in the optical axis direction of the objective lens and/or a direction perpendicular to the optical axis direction.

(Information Processing Unit 5120)

The information processing unit 5120 may acquire, from the microscope apparatus 5100, data (such as imaging data) acquired by the microscope apparatus 5100. The information processing unit 5120 may execute image processing on the imaging data. The image processing may include unmixing and, particularly, spectral unmixing. The unmixing may include processing of extracting data of an optical component with a predetermined wavelength or a predetermined wavelength range from imaging data to generate image data, processing of removing data of an optical component with a predetermined wavelength or a predetermined wavelength range from the imaging data, or the like. In addition, the image processing may include autofluorescence separation processing of separating an autofluorescence component and a pigment component of a tissue section or fluorescence separation processing of separating wavelengths between pigments with mutually-different fluorescent wavelengths. In the autofluorescence separation processing, processing may be performed in which an autofluorescence signal extracted from one of a plurality of samples with the same or similar characteristics is used to remove an autofluorescence component from image information of another sample.

The information processing unit 5120 may transmit data for imaging control to the control unit 5110 and the control unit 5110 having received the data may control imaging by the microscope apparatus 5100 in accordance with the data.

The information processing unit 5120 may be configured as an information processing apparatus such as a general-purpose computer and may include a CPU, a RAM, and a ROM. The information processing unit 5120 may be included inside a casing of the microscope apparatus 5100 or may be provided outside of the casing. In addition, various kinds of processing or functions by the information processing unit 5120 may be realized by a server computer or a cloud connected via a network.

A system of imaging of the living organism-derived specimen S by the microscope apparatus 5100 may be appropriately selected by a person of ordinary skill in the art in accordance with a type of the living organism-derived specimen S, an object of imaging, and the like. Examples of the imaging system will be described below.

An example of the imaging system is as follows. First, the microscope apparatus 5100 may specify an imaging object region. The imaging object region may be specified so as to cover an entire region in which the living organism-derived specimen S is present or specified so as to cover a target portion (a target tissue section, a target cell, or a target lesion) among the living organism-derived specimen S. Next, the microscope apparatus 5100 divides the imaging object region into a plurality of divided regions of a predetermined size and the microscope apparatus 5100 sequentially images each divided region. Accordingly, an image of each divided region is acquired.

Figure 10:
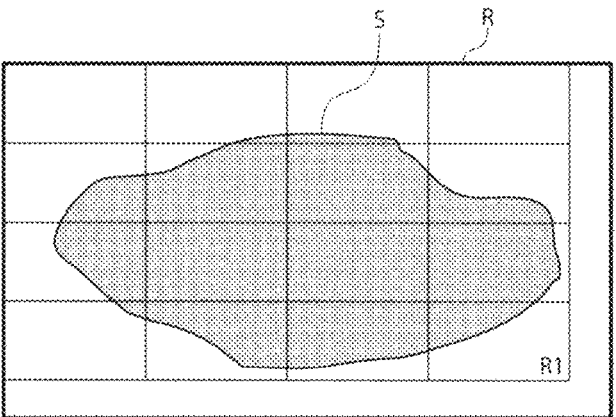
FIG. 10 is a diagram showing an example of an imaging method.

As shown in FIG. 10, the microscope apparatus 5100 specifies an imaging object region R that covers the entire living organism-derived specimen S. In addition, the microscope apparatus 5100 divides the imaging object region R into 16 divided regions. Furthermore, the microscope apparatus 5100 may image a divided region R1 and, next, image any of the regions included in the imaging object region R such as a region adjacent to the divided region R1. In addition, imaging of divided regions is performed until there are no more divided regions that have not been imaged. Note that regions outside of the imaging object region R may also be imaged based on captured image information of the divided regions.

In order to image a next divided region after imaging a given divided region, a positional relationship between the microscope apparatus 5100 and the specimen mounting unit 5104 is adjusted. The adjustment may be performed by moving the microscope apparatus 5100, moving the specimen mounting unit 5104, or moving both the microscope apparatus 5100 and the specimen mounting unit 5104. In this example, the imaging apparatus that images each divided region may be a two-dimensional imaging element (an area sensor) or a one-dimensional imaging element (a line sensor). The signal acquiring unit 5103 may image each divided region via the optical unit 5102. In addition, imaging of each divided region may be continuously performed while moving the microscope apparatus 5100 and/or the specimen mounting unit 5104 or a movement of the microscope apparatus 5100 and/or the specimen mounting unit 5104 may be stopped when imaging each divided region. The imaging object region may be divided so that parts of the respective divided regions overlap with each other or the imaging object region may be divided so that parts of the respective divided regions do not overlap with each other. Each divided region may be imaged a plurality of times by changing imaging conditions such as a focal length and/or an exposure time.

In addition, the information processing apparatus may generate image data of a wider region by stitching a plurality of adjacent divided regions. By performing the stitching processing over the entire imaging object region, an image of a wider region can be acquired with respect to the imaging object region. In addition, image data of a lower resolution may be generated from an image of a divided region or an image having been subjected to stitching processing.

Another example of the imaging system is as follows. First, the microscope apparatus 5100 may specify an imaging object region. The imaging object region may be specified so as to cover an entire region in which the living organism-derived specimen S is present or specified so as to cover a target portion (a target tissue section, a target cell, or a target lesion) among the living organism-derived specimen S. Next, the microscope apparatus 5100 images a region (also referred to as a "divided scan region") that constitutes a part of the imaging object region by scanning in one direction (also referred to as a "scan direction") on a plane perpendicular to the optical axis. When a scan of the divided scan region is completed, next, a divided scan region adjacent to the scan region is scanned. These scan operations are repeated until the entire imaging object region is imaged.

Figure 11:
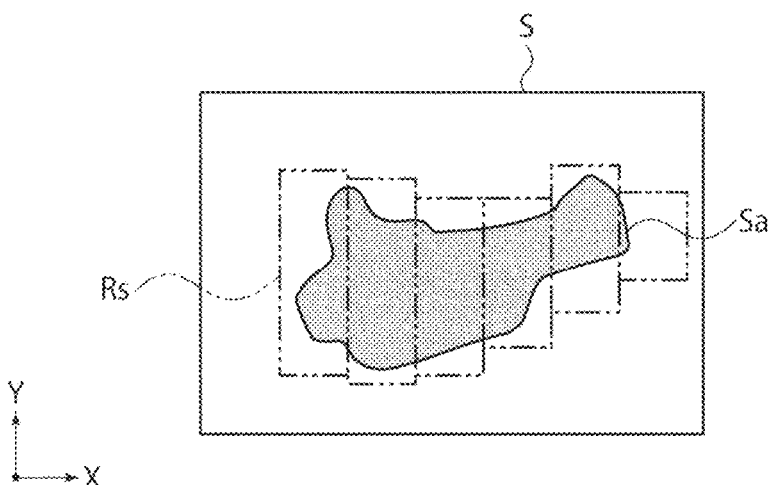
FIG. 11 is a diagram showing an example of an imaging method.

As shown in FIG. 11, the microscope apparatus 5100 specifics a region (a gray portion) where a tissue section is present among the living organism-derived specimen S as an imaging object region Sa. In addition, the microscope apparatus 5100 scans a divided scan region Rs among the imaging object region Sa in a Y-axis direction. When the scan of the divided scan region Rs is completed, the microscope apparatus 5100 next scans a divided scan region that is adjacent in an X-axis direction. These operations are repeated until scans are completed with respect to the entire imaging object region Sa.

In order to scan each divided scan region and to image a next divided scan region after imaging a given divided scan region, a positional relationship between the microscope apparatus 5100 and the specimen mounting unit 5104 is adjusted. The adjustment may be performed by moving the microscope apparatus 5100, moving the specimen mounting unit 5104, or moving both the microscope apparatus 5100 and the specimen mounting unit 5104. In this example, the imaging apparatus that images each divided scan region may be a one-dimensional imaging element (a line sensor) or a two-dimensional imaging element (an area sensor). The signal acquiring unit 5103 may image each divided region via a magnifying optical system. In addition, imaging of each divided scan region may be continuously performed while moving the microscope apparatus 5100 and/or the specimen mounting unit 5104. The imaging object region may be divided so that parts of the respective divided scan regions overlap with each other or the imaging object region may be divided so that parts of the respective divided scan regions do not overlap with each other. Each divided scan region may be imaged a plurality of times by changing imaging conditions such as a focal length and/or an exposure time.

In addition, the information processing apparatus may generate image data of a wider region by stitching a plurality of adjacent divided scan regions. By performing the stitching processing over the entire imaging object region, an image of a wider region can be acquired with respect to the imaging object region. In addition, image data of a lower resolution may be generated from an image of a divided scan region or an image having been subjected to stitching processing.

[Biological Specimen Analysis Apparatus 6100]

Figure 12:
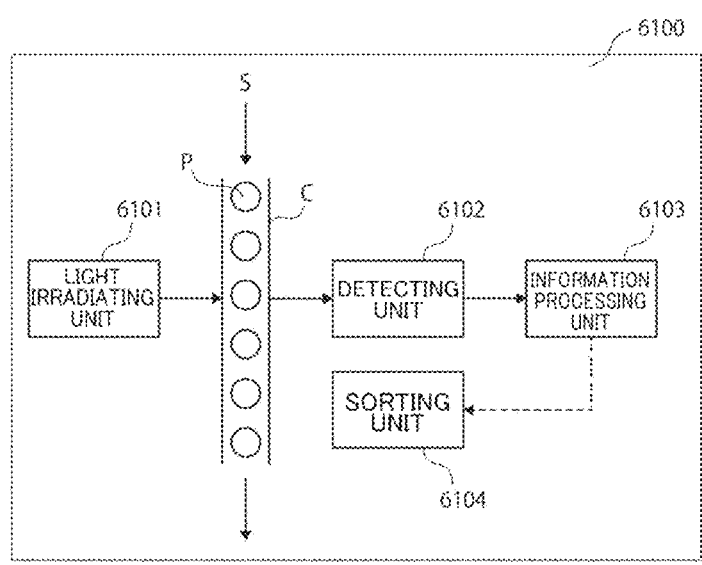
FIG. 12 is a diagram schematically showing an overall configuration of a biological specimen analysis apparatus 6100.

FIG. 12 shows a configuration example of the biological specimen analysis apparatus 6100 according to the present technique. The biological specimen analysis apparatus 6100 shown in FIG. 12 includes a light irradiating unit 6101 that irradiates a biological specimen S flowing through a flow channel C with light, a detecting unit 6102 that detects light generated by irradiating the biological specimen S with light, and an information processing unit 6103 that processes information related to light detected by the detecting unit 6102. Examples of the biological specimen analysis apparatus 6100 include a flow cytometer and an imaging cytometer. The biological specimen analysis apparatus 6100 may include a sorting unit 6104 that sorts specific biological particles P in the biological specimen S. Examples of the biological specimen analysis apparatus 6100 that includes the sorting unit include a cell sorter.

(Biological Specimen S)

The biological specimen S may be a liquid specimen including the biological particles P. The biological particles P are, for example, cells or non-cellular biological particles. The cells may be living cells and more specific examples can include blood cells such as red blood cells and white blood cells and germ cells such as sperm and fertilized eggs. In addition, the cells may be directly collected from a sample such as whole blood or may be cultured cells acquired after culture. Examples of the non-cellular biological particles include extracellular vesicles and, particularly, exosomes and microvesicles. The biological particles P may be labeled by one or a plurality of labeled substances (such as pigments (particularly, fluorochromes) and fluorochrome-labeled antibodies). The biological specimen analysis apparatus according to the present disclosure may analyze particles other than the biological particles P and beads or the like may be analyzed for calibration or the like.

(Flow Channel C)

The flow channel C is configured so that the biological specimen S flows therethrough. In particular, the flow channel C is configured so that a flow in which the biological particles P included in the biological specimen S are approximately lined up in a row is formed. A flow channel structure including the flow channel C may be designed so that a laminar flow is formed. In particular, the flow channel structure is designed so that a laminar flow is formed in which a flow (a sample flow) of the biological specimen S is enclosed by a flow of a sheath liquid. The design of the flow channel structure may be appropriately selected by a person of ordinary skill in the art and a known design may be adopted. The flow channel C may be formed in a flow channel structure such as a microchip (a chip having a flow channel in an order of micrometers) or a flow cell. A width of the flow channel C is 1 mm or less and may particularly be 10 μm or more and 1 mm or less. The flow channel C and the flow channel structure including the flow channel C may be formed of a material such as plastic or glass.

The biological specimen analysis apparatus 6100 according to the present technique is configured so that the biological specimen S flowing inside the flow channel C and, in particular, the biological particles P inside the biological specimen S are irradiated with light from the light irradiating unit 6101. The biological specimen analysis apparatus 6100 according to the present technique can be configured such that an interrogation point of light with respect to the biological specimen S is inside a flow channel structure in which the flow channel C is formed or configured such that the interrogation point of light is outside the flow channel structure. Examples of the former include a configuration in which the flow channel C inside a microchip or a flow cell is irradiated with the light. In the latter case, the biological particles P after exiting the flow channel structure (in particular, a nozzle portion thereof) may be irradiated with the light and examples include a Jet-in-Air flow cytometer.
(Light Irradiating Unit 6101)

The light irradiating unit 6101 includes a light source unit that emits light and a guiding optical system that guides the light to an interrogation point. The light source unit includes one or a plurality of light sources. Examples of a type of the light sources include a laser light source and an LED light source. A wavelength of light emitted from each light source may be a wavelength of any of ultraviolet light, visible light, and infrared light. The guiding optical system includes an optical component such as a beam splitter group, a mirror group, or an optical fiber. In addition, the guiding optical system may include a lens group for collecting light and includes, for example, an objective lens. There may be one or a plurality of interrogation points where the biological specimen S and light intersect with each other. The light irradiating unit 6101 may be configured to collect, with respect to one interrogation point, light radiated from one light source or a plurality of different light sources.
(Detecting Unit 6102)

The detecting unit 6102 includes at least one photodetector that detects light created by light irradiation to the biological particles P. The light to be detected is, for example, fluorescent light or scattered light (for example, one or more of forward-scattered light, back-scattered light, and side-scattered light). Each photodetector includes one or more light-receiving elements and has, for example, a light-receiving element array. Each photodetector may include, as the light-receiving element, one or a plurality of PMTs (photomultiplier tubes) and/or photodiodes such as APDs and MPPCs. The photodetector includes, for example, a PMT array in which a plurality of PMTs are arranged in a one-dimensional direction. In addition, the detecting unit 6102 may include an imaging element such as a CCD or a CMOS. Using the imaging element, the detecting unit 6102 may acquire an image (for example, a bright-field image, a dark-field image, a fluorescent image, and the like) of the biological particles P.

The detecting unit 6102 includes a detecting optical system that causes light with a predetermined detection wavelength to reach a corresponding photodetector. The detecting optical system includes a spectroscopic unit such as a prism or a diffraction grating or a wavelength separating unit such as a dichroic mirror or an optical filter. The detecting optical system is configured to spectrally disperse light created by light irradiation of the biological particles P so that the spectrally-dispersed light is detected by a plurality of photodetectors of which number is larger than the number of fluorochromes by which the biological particles P are labeled. A flow cytometer including such a detecting optical system is referred to as a spectral flow cytometer. In addition, for example, the detecting optical system is configured to separate light corresponding to a fluorescent wavelength of a specific fluorochrome from light created by light irradiation of the biological particles P and cause a corresponding photodetector to detect the separated light.

In addition, the detecting unit 6102 may include a signal processing unit that converts an electric signal obtained by a photodetector into a digital signal. The signal processing unit may include an AD converter as an apparatus that performs the conversion. The digital signal obtained by the conversion by the signal processing unit may be transmitted to the information processing unit 6103. The digital signal may be handled by the information processing unit 6103 as data related to light (hereinafter, also referred to as "optical data"). The optical data may be optical data including, for example, fluorescence data. More specifically, the optical data may be light intensity data and the light intensity may be light intensity data (which may include feature amounts such as area, height, and width) of light including fluorescence.
(Information Processing Unit 6103)

The information processing unit 6103 includes, for example, a processing unit that executes processing of various kinds of data (for example, optical data) and a storage unit that stores the various kinds of data. When optical data corresponding to a fluorochrome is acquired from the detecting unit 6102, the processing unit may perform fluorescence leakage correction (compensation processing) on light intensity data. In addition, in the case of a spectral flow cytometer, the information processing unit 6103 executes fluorescence separation processing with respect to optical data and acquires light intensity data corresponding to a fluorochrome.

The fluorescence separation processing may be performed according to, for example, an unmixing method described in JP 2011-232259A. When the detecting unit 6102 includes an imaging element, the information processing unit 6103 may acquire morphological information of the biological particles P based on an image acquired by the imaging element. The storage unit may be configured to store acquired optical data. The storage unit may be further configured to store spectral reference data to be used in the unmixing.

When the biological specimen analysis apparatus 6100 includes the sorting unit 6104 to be described later, the information processing unit 6103 may execute a determination as to whether or not the biological particles Pare to be sorted based on optical data and/or morphological information. In addition, the information processing unit 6103 may control the sorting unit 6104 based on a result of the determination and sorting of the biological particles P by the sorting unit 6104 may be performed.

The information processing unit 6103 may be configured to be capable of outputting various kinds of information (for example, optical data and images). For example, the information processing unit 6103 may output various kinds of data (for example, a two-dimensional plot or a spectral plot) generated based on the optical data. In addition, the information processing unit 6103 may be configured to accept input of various kinds of data and may accept, for example, gating on a plot by the user. The information processing unit 6103 may include an output unit (for example, a display) or an input unit (for example, a keyboard) to execute the output or the input.

The information processing unit 6103 may be configured as a general-purpose computer and configured as, for example, an information processing apparatus including a CPU, a RAM, and a ROM. The information processing unit 6103 may be included in a casing in which the light irradiating unit 6101 and the detecting unit 6102 are provided or may be present outside of the casing. In addition, various kinds of processing or functions by the information processing unit 6103 may be realized by a server computer or a cloud connected via a network.

(Sorting Unit 6104)

The sorting unit 6104 executes sorting of the biological particles P in accordance with a result of the determination by the information processing unit 6103. A method of the sorting may be a method of generating droplets containing the biological particles P by vibration, applying an electric charge to a droplet that is a sorting object, and controlling a travel direction of the droplet with an electrode. The method of sorting may be a method in which sorting is performed by controlling a travel direction of the biological particles P in a flow channel structure. The flow channel structure is provided with, for example, a control mechanism due to pressure (injection or absorption) or an electric charge. Examples of the flow channel structure include a chip in which a flow channel C has a flow channel structure where the flow channel C branches to a recovery flow channel and a waste liquid flow channel on a downstream side and which specific biological particles P are recovered into the recovery flow channel (for example a chip described in JP 2020-76736A.

EXAMPLES

Hereinafter, the present invention will be described in more detail based on examples. The examples to be described below show representative examples of the present invention, and the scope of the present invention is not to be narrowly construed on the basis of the examples.

First Experimental Example

In a first experimental example, a second signal group was acquired when binding molecules of a same type having been labeled by different labeled molecules are respectively reacted with a target molecule.

Specifically, fluorescent immunostaining was performed using: a paraffin-embedded tissue section of human mammary gland cancer as an example of a target molecule; AF488, AF647, AF700, and PE (Phycoerythrin) of the fluorochrome AlexaFluor (registered trademark) series as examples of a labeled molecule; and an anti-Pan-Cytokeratin antibody (Clone: AE1/AE3) as an example of a binding molecule.

Figure 13:
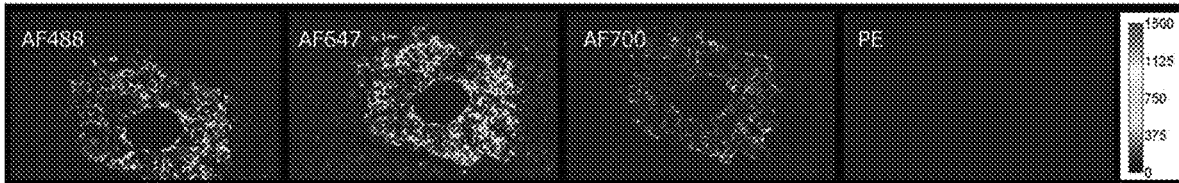
FIG. 13 is a photograph being a substitute for a diagram showing a result of fluorescent immunostaining performed in a first experimental example using: a paraffin-embedded tissue section of human mammary gland cancer as an example of a target molecule; AF488, AF647, AF700, and PE (Phycoerythrin) of the fluorochrome AlexaFluor (registered trademark) series as examples of a labeled molecule; and an anti-Pan-Cytokeratin antibody (Clone: AE1/AE3) as an example of a binding molecule.

A result of the fluorescent immunostaining is shown in FIG. 13. As shown in FIG. 13, it was confirmed that, when binding molecules of a same type having been labeled by different labeled molecules are respectively reacted with a target molecule, reactivity is affected.

28

Second Experimental Example

In a second experimental example, a first signal group and a second signal group were acquired and, when using a plurality of different binding molecules having been labeled by different labeled molecules, reactivity of a target molecule and each of the plurality of different binding molecules was calculated.

Specifically, fluorescent immunostaining was performed using: a formalin-fixed and paraffin-embedded tissue section of human amygdala as an example of a target molecule; AF488, AF555, AF594, and AF647 of the fluorochrome AlexaFluor (registered trademark) series as examples of a labeled molecule; and a CD3 antibody, a CD5 antibody, and a CD7 antibody as examples of a binding molecule.

(1) Acquisition of First Signal Group

Captured images were obtained when reacting each of a plurality of different binding molecules CD3 antibody, CD5 antibody, and CD7 antibody labeled with the labeled molecule AF647 of a same type with a target molecule. In addition, captured images were obtained when respectively reacting the binding molecule CD3 antibody labeled with AF488, the binding molecule CD3 antibody labeled with AF555, and the binding molecule CD5 antibody labeled with AF594 with a target molecule. The number of binding molecules were calculated from each of the obtained captured images. The calculated numbers of binding molecules are shown in Table 4 below.

TABLE 4

| [NUMBER OF BINDING MOLECULES] | | | | | |
|---|---|---|---|---|---|
| | | LABELED MOLECULE | | | |
| | | AF488 | AF555 | AF594 | AF647 |
| BINDING | CD3 | 25.2 | 15.2 | | 3.40 |
| MOLECULE | CD5 | | | 9.62 | 1.92 |
| | CD7 | | | | 29.5 |

(2) Acquisition of Second Signal Group

Captured images were obtained when respectively reacting the binding molecule CD3 antibody of a same type labeled with different labeled molecules AF488, AF555, and AF647, with a target molecule. In addition, captured images were obtained when respectively reacting the binding molecule CD3 antibody labeled with AF488, the binding molecule CD3 antibody labeled with AF555, and the binding molecule CD5 antibody labeled with AF594, with a target molecule. A fluorescence intensity/autofluorescence ratio was calculated from each obtained captured image. The calculated fluorescence intensity/autofluorescence ratios are shown in Table 5 below.

TABLE 5

| [FLUORESCENCE INTENSITY/AUTOFLUORESCENCE RATIO] | | | | | |
|---|---|---|---|---|---|
| | | LABELED MOLECULE | | | |
| | | AF488 | AF555 | AF594 | AF647 |
| BINDING | CD3 | 0.739 | 2.41 | | 4.58 |
| MOLECULE | CD5 | | | 0.320 | 1.48 |
| | CD7 | | | | 18.0 |

(3) Calculation of Reactivity Index

Indexes of reactivity were calculated using the numerical values in Table 4 and Table 5. In the present experimental example, a fluorescence intensity/autofluorescence ratio was used as an index of reactivity. Specifically, the index of reactivity index was calculated using the following expression.

> Reactivity index calculated value=(number of anti-bodies with same-type labels of calculation object binding molecule/number of antibodies with same-type labels of reference binding molecule)×[fluorescence intensity/autofluorescence ratio] of reference binding molecule of calculation object fluorochrome For example, the reactivity index (fluorescence intensity/autofluorescence ratio) of CD7 labeled with AF488 was calculated as follows.

Number of antibodies with same-type labels of calculation object binding molecule: number of antibodies of AF647CD7=29.5 (Table 4)

Number of antibodies with same-type labeled antibody of reference binding molecule: number of antibodies of AF647CD3=3.40 (Table 4)

[Fluorescence intensity/autofluorescence ratio] of reference binding molecule of calculation object fluorochrome: [fluorescence intensity/autofluorescence ratio] of AF488CD3=0.739

(29.5/3.40)×0.739≈6.42

(4) Calculation Result of Reactivity Index

A calculation result of the reactivity indexes is shown in Table 6 below.

TABLE 6

[INDEX (FLUORESCENCE INTENSITY/AUTOFLUORESCENCE RATIO)]

| | | LABELED MOLECULE | | | |
|---|---|---|---|---|---|
| | | AF488 | AF555 | AF594 | AF647 |
| BINDING MOLECULE | CD3 | 0.739 | 2.41 | (0.567) | 4.58 |
| | CD5 | (0.416) | (1.36) | 0.320 | (2.58) |
| | CD7 | (6.42) | (20.9) | (4.92) | (39.8) |

CALCULATED VALUE IN ( )

(5) Selection of Combination of Labeled Molecule and Binding Molecule Based on the calculated reactivity indexes, a selection of a combination of a labeled molecule and a binding molecule was performed. In the second experimental example, as an example of selection, selection was performed so that labels were assigned in a descending order of a signal to binding molecules in an ascending order of a value of the first signal group.

Specifically, first, in Table 4, since a smallest value of the first signal in AF647 is 1.92 of AF647CD5 and a largest value of the reactivity index calculated value of CD5 is 2.58 of AF647CD5, the label AF647 is assigned to the binding molecule CD5.

In Table 4, although a next smallest value of the first signal in AF647 is 3.40 of AF647CD3 and the largest value of the reactivity index calculated value of CD3 is 4.58 of AF647CD3, since AF647 is already assigned to CD5, 2.41 of AF555CD3 indicating a next highest value is selected and the label AF555 is assigned to the binding molecule CD3.

In Table 4, although a next smallest value of the first signal in AF647 is 29.5 of AF647CD7, the largest value of the reactivity index calculated value of CD7 is 39.8 of AF647CD7, and a next largest value of the reactivity index calculated value of CD7 is 20.9 of AF555CD7, since both are already assigned, 6.42 of AF488CD7 indicating a next highest value is selected and the label AF488 is assigned to CD7.

From the above, AF488CD7, AF555CD3, and AF647CD5 are selected as combinations of a labeled molecule and a binding molecule.

(6) Staining Confirmation

Figure 14:
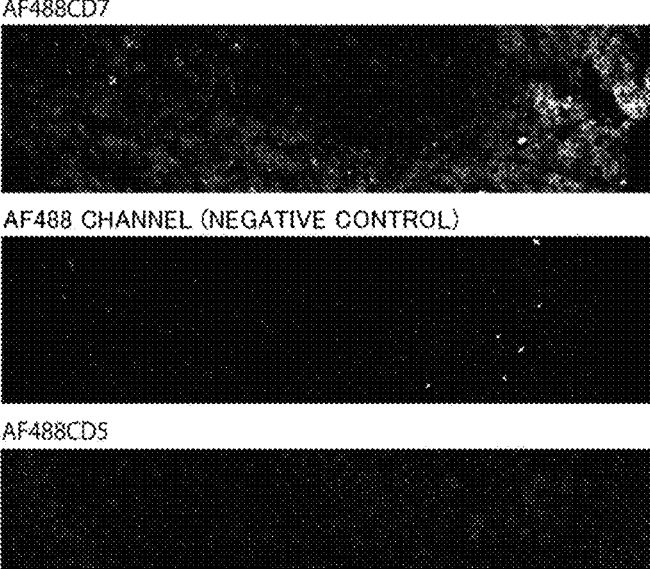

Fluorescent immunostaining of a formalin-fixed and paraffin-embedded tissue section of human amygdala was performed using combinations of a labeled molecule and a binding molecule selected as described above. Images of respective fluorescently-labeled antibodies in a multi-stained image are shown in FIGS. 14 to 16. An image of each fluorescent label in an unstained sample is also shown as negative control. With respect to the label AF488, a stained image of AF488CD5 being a combination not selected due to the reactivity index calculated value being a low value is also displayed for reference.

(7) Quantitative Determination of Number of Antibodies

The number of antibodies was also calculated based on a multi-stained image using the combinations of a labeled molecule and a binding molecule selected above and an image of each fluorescent label in the unstained sample. Calculation results are shown in Table 7 and Table 8 below.

TABLE 7

[RESULT OF QUANTITATIVE DETERMINATION OF NUMBER OF ANTIBODIES IN SELECTED COMBINATION OF LABELED MOLECULE AND BINDING MOLECULE]

| | | LABELED MOLECULE | | |
|---|---|---|---|---|
| | | AF488 | AF555 | AF647 |
| BINDING MOLECULE | CD3 | — | 20.1 | — |
| | CD5 | — | — | 5.11 |
| | CD7 | 5.90 | — | — |

TABLE 8

[RESULT OF QUANTITATIVE DETERMINATION OF NUMBER OF ANTIBODIES IN UNSTAINED SPECIMEN (NEGATIVE CONTROL)]

| | | LABELED MOLECULE | | |
|---|---|---|---|---|
| | | AF488 | AF555 | AF647 |
| BINDING MOLECULE | CD3 | — | 0.878 | — |
| | CD5 | — | — | 1.53 |
| | CD7 | 3.21 | — | — |

(8) Consideration

As shown in FIGS. 14 to 16, it was proven that performing fluorescent immunostaining using the selected combinations of a labeled molecule and a binding molecule results in values which are higher than negative control and which are all detectable. In addition, as shown in FIG. 14, with respect to AF488CD5 being a combination not selected due to a reactivity index calculated value thereof being a low value, since a signal is a lower value than AF647CD5 having been selected and detection is difficult, it was proven that the combination of AF488CD5 is inadequate.

Third Experimental Example

In a third experimental example, selection of combinations of a labeled molecule and a binding molecule was performed by a different method from the second experimental example.

The selection of combinations of a labeled molecule and a binding molecule was performed based on the reactivity indexes calculated in the second experimental example. In the third experimental example, as an example of selection, selection was performed so that fluorescent labels on a short wavelength side were sequentially assigned to binding molecules in a descending order of a value of the first signal group. When there were a plurality of candidates, a combination with a higher panel design index calculated value was selected.

Specifically, first, in Table 4, since a descending order of values of the first signal in AF647 was CD7, CD3, and CD5 and the values were respectively 29.5, 3.40, and 1.92, AF488 and AF555 being fluorochromes on a short wavelength side were respectively assigned in a descending order of values of the first signal, in which case CD7 was assigned to AF488 and CD3 was assigned to AF555. While AF594 and AF647 can be assigned to CD5, since a reactivity index calculated value of AF594CD5 was 0.320 and a reactivity index calculated value of AF647CD5 was 2.58, AF647CD5 with the higher reactivity index calculated value was selected.

From the above, AF488CD7, AF555CD3, and AF647CD5 were selected as combinations of a labeled molecule and a binding molecule.

In the present technique, the following configurations can also be adopted.

(1)
An information processing apparatus, including:
a processing unit configured to calculate, based on a signal derived from a sample including a biological specimen, when using a plurality of different binding molecules labeled by different labeled molecules, reactivity between a target molecule and each of the plurality of different binding molecules,
wherein
the signal includes:
a first signal group acquired when each of a plurality of different binding molecules having been labeled by a labeled molecule of a same type is reacted with a target molecule, and
a second signal group acquired when each of binding molecules of a same type having been labeled by different labeled molecules is reacted with a target molecule.

(2)
The information processing apparatus according to (1), wherein the number of binding molecules and/or a fluorescence intensity labeled by the binding molecules is calculated as an index of the reactivity.

(3)
The information processing apparatus according to (2), wherein the fluorescence intensity is calculated from one or more numerical values selected from an excitation efficiency, a quantum yield, an absorption efficiency, and a ratio of fluorescence labeling (F/P value).

(4)
The information processing apparatus according to any one of (1) to (3), wherein the signal includes at least one of a signal, a specific signal/background, and a specific signal/non-specific signal.

(5)
The information processing apparatus according to any one of (1) to (3), wherein the processing unit is configured to calculate a background in each detection channel based on a third signal acquired when using negative control.

(6)
The information processing apparatus according to (4), wherein the processing unit is configured to calculate a leakage of an autofluorescence signal and/or a leakage of a signal derived from another labeled molecule.

(7)
The information processing apparatus according to any one of (1) to (6), wherein the processing unit is configured to calculate reactivity with a target molecule with respect to a combination of a labeled molecule and a binding molecule of which a measurement has not been actually performed.

(8)
The information processing apparatus according to any one of (4) to (7), wherein the processing unit is configured to select a combination of a labeled molecule and a binding molecule of which the specific signal/background equals or exceeds a threshold.

(9)
The information processing apparatus according to any one of (4) to (8), wherein the processing unit is configured to select a combination of a labeled molecule and a binding molecule which maximizes a sum of the specific signal/background.

(10)
The information processing apparatus according to any one of (2) to (9), wherein the processing unit is configured to select a combination of a labeled molecule and a binding molecule which maximizes a sum of differences between a signal of the fluorescence intensity and a background of the fluorescence intensity.

(11)
The information processing apparatus according to any one of (2) to (10), wherein the processing unit is configured to select a combination of a labeled molecule and a binding molecule based on a magnitude of a signal of fluorescence intensity.

(12)
The information processing apparatus according to any one of (2) to (10), wherein the processing unit is configured to select a combination of a labeled molecule and a binding molecule so that labels are to be assigned in a descending order of a signal of fluorescence intensity to binding molecules in an ascending order of a value of the first signal group.

(13)
The information processing apparatus according to any one of (2) to (10), wherein the processing unit is configured to select a combination of a labeled molecule and a binding molecule so that labels are to be assigned in an ascending order of a length of a detection wavelength to binding molecules in a descending order of a value of the first signal group.

(14)
The information processing apparatus according to any one of (1) to (13), further including a presenting unit configured to present, to a user, support information on a combination of a binding molecule and a labeled molecule based on the calculated reactivity.

(15)
The information processing apparatus according to any one of (1) to (14), further including an evaluating unit configured to estimate a significance of a binding molecule and/or a labeled molecule with respect to a target molecule based on image information.

(16)
The information processing apparatus according to any one of (1) to (15), wherein the first signal group and the second signal group are detection amounts having been standardized using at least one selected from excitation power density, exposure time, and detection device sensitivity.

(17)

A biological specimen analysis method, including the steps of:

acquiring a signal derived from a sample including a biological specimen; calculating, based on the signal, when using a plurality of different binding molecules labeled by different labeled molecules, reactivity between a target molecule and each of the plurality of different binding molecules; and outputting the reactivity, wherein the signal includes:

a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule.

(18)

An information processing system, including:

an information processing apparatus including:

a signal acquiring unit configured to acquire a signal derived from a sample including a biological specimen;

a processing unit configured to calculate, based on the signal, when using a plurality of different binding molecules labeled by different labeled molecules, reactivity between a target molecule and each of the plurality of different binding molecules;

an output unit configured to output the reactivity, the signal including:

a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule, and a storage apparatus configured to store information calculated by the information processing apparatus.

(19)

The information processing system according to (18), wherein the information processing apparatus takes information stored in the storage apparatus into consideration.

(20)

A biological specimen detection apparatus, including:

a signal acquiring unit configured to acquire a signal derived from a sample including a biological specimen;

a processing unit configured to calculate, based on the signal, when using a plurality of different binding molecules labeled by different labeled molecules, reactivity between a target molecule and each of the plurality of different binding molecules;

an output unit configured to output the reactivity; and a detecting unit configured to detect a signal emitted from a target molecule labeled using a binding molecule which is selected based on the output reactivity and which is labeled by a labeled molecule, wherein the signal includes:

a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule.

(21)

The biological specimen detection apparatus according to (20), further including a labeling unit configured to label a target molecule using a binding molecule which is selected based on the output reactivity and which is labeled by a labeled molecule.

(22)

The biological specimen detection apparatus according to (20) or (21), further including an analyzing unit configured to analyze the sample based on a signal detected by the detecting unit.

(23)

A biological specimen detection system, including:

an information processing apparatus including:

a signal acquiring unit configured to acquire a signal derived from a sample including a biological specimen;

a processing unit configured to calculate, based on the signal, when using a plurality of different binding molecules labeled by different labeled molecules, reactivity between a target molecule and each of the plurality of different binding molecules;

an output unit configured to output the reactivity, the signal including:

a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule, and a detection apparatus configured to detect a signal emitted from a target molecule labeled using a binding molecule which is selected based on the output reactivity and which is labeled by a labeled molecule.

(24)

A computer program for causing a computer to realize:

a signal acquisition function of acquiring a signal derived from a sample including a biological specimen;

a processing function of calculating, based on the signal, when using a plurality of different binding molecules labeled by different labeled molecules, reactivity between a target molecule and each of the plurality of different binding molecules; and an output function of outputting the reactivity, wherein the signal includes:

a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule.

35      36

(25)

A biological specimen detection system, including:

a computer program for causing a computer to realize:

a signal acquisition function of acquiring a signal derived from a sample including a biological specimen;

a processing function of calculating, based on the signal, when using a plurality of different binding molecules labeled by different labeled molecules, reactivity between a target molecule and each of the plurality of different binding molecules; and an output function of outputting the reactivity, the signal including:

a first signal group acquired when each of a plurality of different binding molecules having been labeled by a labeled molecule of a same type is reacted with a target molecule, and a second signal group acquired when each of binding molecules of a same type having been labeled by different labeled molecules is reacted with a target molecule, and a detection apparatus configured to detect a signal emitted from a target molecule labeled using a binding molecule which is selected based on the output reactivity and which is labeled by a labeled molecule.

1 Information processing apparatus
11 Signal acquiring unit
12 Processing unit
13 Evaluating unit
14 Output unit
15 Presenting unit
16 Storage unit
17 Display unit
18, 23 User interface
2 Information processing system
3 Biological specimen detection apparatus
4 Biological specimen detection system
21 Storage apparatus
22 Display apparatus
24 Evaluation apparatus
31, 6102 Detecting unit
41 Detection apparatus
32 Labeling unit
42 Labeling apparatus
33 Analyzing unit
43 Analysis apparatus
5000 Microscopic system
5100 Microscope apparatus
5110 Control unit
5120, 6103 Information processing unit
5101, 6101 Light irradiating unit
5102 Optical unit
5103 Signal acquiring unit
5104 Specimen mounting unit
S Living organism-derived specimen, biological specimen
R, Sa Imaging object region
R1 Divided region
Rs Divided scan region
6100 Biological specimen analysis apparatus
C Flow channel
P Biological particle
6104 Sorting unit

The invention claimed is:

1. An information processing apparatus, comprising:

A processor configured to calculate, based on a signal derived from a sample including a biological specimen, when using a plurality of different binding molecules labeled by different labeled molecules, reactivity between a target molecule and each of the plurality of different binding molecules, wherein the signal includes:

a first signal group acquired when each of a plurality of different binding molecules having been labeled by a labeled molecule of a same type is reacted with the target molecule, and a second signal group acquired when each of a binding molecule of a same type having been labeled by different labeled molecules is reacted with the target molecule; and wherein the processor is configured to select a combination of the labeled molecule and the binding molecule by one or more methods selected from (a) to (f) below:

(a) select the combination of the labeled molecule and the binding molecule of which a specific signal/background equals or exceeds a threshold;

(b) select the combination of the labeled molecule and the binding molecule which maximizes a sum of a specific signal/background;

(c) select the combination of the labeled molecule and the binding molecule which maximizes a sum of differences between a signal of fluorescence intensity and a background of the fluorescence intensity;

(d) select the combination of the labeled molecule and the binding molecule based on a magnitude of a signal of fluorescence intensity;

(e) select the combination of the labeled molecule and the binding molecule so that labels are to be assigned in a descending order of the signal of fluorescence intensity to binding molecules in an ascending order of a value of the first signal group; and (f) select the combination of the labeled molecule and the binding molecule so that labels are to be assigned in an ascending order of a length of a detection wavelength to binding molecules in a descending order of a value of the first signal group; and wherein in each of the one or more selected methods from (a) to (f), the significance of the binding molecule and/or the labeled molecule with respect to the target molecule is estimated by determining whether or not to raise a luminance in accordance with a type of the binding molecule or the labeled molecule, considering how the threshold is to be set, and lowering a background to enable an object signal to be picked up more easily when the object signal is weak.

2. The information processing apparatus according to claim 1, wherein the processor is configured to calculate the number of binding molecules and/or a fluorescence intensity labeled by the binding molecules as an index of the reactivity.

3. The information processing apparatus according to claim 2, wherein the fluorescence intensity is calculated from one or more numerical values selected from an excitation efficiency, a quantum yield, an absorption efficiency, and a ratio of fluorescence labeling (F/P value).

4. The information processing apparatus according to claim 1, wherein the signal includes at least one of the signal, the specific signal/background, and a specific signal/non-specific signal.

5. The information processing apparatus according to claim 1, wherein the processor is configured to calculate a background in each detection channel based on a third signal acquired when using negative control.

6. The information processing apparatus according to claim 2, wherein the processor is configured to calculate a leakage of an autofluorescence signal and/or a leakage of a signal derived from another labeled molecule.

7. The information processing apparatus according to claim 1, wherein the processor is configured to calculate reactivity with the target molecule with respect to a combination of the labeled molecule and the binding molecule of which a measurement has not been actually performed.

8. The information processing apparatus according to claim 1, further comprising an image evaluator configured to estimate a significance of the binding molecule and/or the labeled molecule with respect to the target molecule based on image information.

9. The information processing apparatus according to claim 1, wherein the first signal group and the second signal group are detection amounts having been standardized using at least one selected from excitation power density, exposure time, and detection device sensitivity.

10. A biological specimen analysis method, comprising the steps of:

acquiring a signal derived from a sample including a biological specimen; calculating, based on the signal, when using a plurality of different binding molecules labeled by different labeled molecules, reactivity between a target molecule and each of the plurality of different binding molecules; and outputting the reactivity, wherein the signal includes:

a first signal group acquired when each of a plurality of different binding molecules having been labeled by a labeled molecule of a same type is reacted with the target molecule, and a second signal group acquired when each of a binding molecule of a same type having been labeled by different labeled molecules is reacted with the target molecule; and wherein the processor is configured to select a combination of the labeled molecule and the binding molecule by one or more methods selected from (a) to (f) below:

(a) select the combination of the labeled molecule and the binding molecule of which a specific signal/background equals or exceeds a threshold;

(b) select the combination of the labeled molecule and the binding molecule which maximizes a sum of a specific signal/background;

(c) select the combination of the labeled molecule and the binding molecule which maximizes a sum of differences between a signal of fluorescence intensity and a background of the fluorescence intensity;

(d) select the combination of the labeled molecule and the binding molecule based on a magnitude of a signal of fluorescence intensity;

(e) select the combination of the labeled molecule and the binding molecule so that labels are to be assigned in a descending order of the signal of fluorescence intensity to binding molecules in an ascending order of a value of the first signal group; and (f) select the combination of the labeled molecule and the binding molecule so that labels are to be assigned in an ascending order of a length of a detection wavelength to binding molecules in a descending order of a value of the first signal group; and wherein in each of the one or more selected methods from (a) to (f), the significance of the binding molecule and/or the labeled molecule with respect to the target molecule is estimated by determining whether or not to raise a luminance in accordance with a type of the binding molecule or the labeled molecule, considering how the threshold is to be set, and lowering a background to enable an object signal to be picked up more easily when the object signal is weak.

11. A biological specimen detection apparatus, comprising:

A sample signal acquirer configured to acquire a signal derived from a sample including a biological specimen;

an information processing apparatus including:

a processor configured to calculate, based on the signal, when using a plurality of different binding molecules labeled by different labeled molecules, reactivity between a target molecule and each of the plurality of different binding molecules;

a detection process output router configured to output the reactivity; and a signal detector configured to detect a signal emitted from the target molecule labeled using a binding molecule which is selected based on the output reactivity and which is labeled by a labeled molecule, wherein the signal includes:

a first signal group acquired when each of a plurality of different binding molecules having been labeled by a labeled molecule of a same type is reacted with the target molecule, and a second signal group acquired when each of the binding molecules of a same type having been labeled by different labeled molecules is reacted with the target molecule; and wherein the processor is configured to select a combination of the labeled molecule and the binding molecule by one or more methods selected from (a) to (f) below:

(a) select the combination of the labeled molecule and the binding molecule of which a specific signal/background equals or exceeds a threshold;

(b) select the combination of the labeled molecule and the binding molecule which maximizes a sum of a specific signal/background;

(c) select the combination of the labeled molecule and the binding molecule which maximizes a sum of differences between a signal of fluorescence intensity and a background of the fluorescence intensity;

(d) select the combination of the labeled molecule and the binding molecule based on a magnitude of a signal of fluorescence intensity;

(e) select the combination of the labeled molecule and the binding molecule so that labels are to be assigned in a descending order of the signal of fluorescence intensity to binding molecules in an ascending order of a value of the first signal group; and (f) select the combination of the labeled molecule and the binding molecule so that labels are to be assigned in an ascending order of a length of a detection wavelength to binding molecules in a descending order of a value of the first signal group; and wherein in each of the one or more selected methods from (a) to (f), the significance of the binding molecule and/or the labeled molecule with respect to the target molecule is estimated by determining whether or not to raise a luminance in accordance with a type of the binding molecule or the labeled molecule, considering how the threshold is to be set, and lowering a background to enable an object signal to be picked up more easily when the object signal is weak.

12. The biological specimen detection apparatus according to claim 11, further comprising a combination reactivity presentation processor configured to present, to a user, support information on a combination of the binding molecule and the labeled molecule based on the calculated reactivity.

13. The biological specimen detection apparatus according to claim 11, further comprising a target molecule labeler configured to label the target molecule using the binding molecule which is selected based on the output reactivity and which is labeled by the labeled molecule.

14. The biological specimen detection apparatus according to claim 11, further comprising a sample analyzer configured to analyze the sample based on the signal detected by the signal detector.

15. A biological specimen detection system, comprising:
an information processing apparatus including:
a sample signal acquirer configured to acquire a signal derived from a sample including a biological specimen;
a processor configured to calculate, based on the signal, when using a plurality of different binding molecules labeled by different labeled molecules, reactivity between a target molecule and each of the plurality of different binding molecules;
a detection process output router configured to output the reactivity, the signal including:
a first signal group acquired when each of a plurality of different binding molecules having been labeled by a labeled molecule of a same type is reacted with the target molecule, and
a second signal group acquired when each of a binding molecule of a same type having been labeled by different labeled molecules is reacted with the target molecule; and
wherein the processor is configured to select a combination of the labeled molecule and the binding molecule by one or more methods selected from (a) to (f) below:
(a) select the combination of the labeled molecule and the binding molecule of which a specific signal/background equals or exceeds a threshold;

(b) select the combination of the labeled molecule and the binding molecule which maximizes a sum of a specific signal/background;
(c) select the combination of the labeled molecule and the binding molecule which maximizes a sum of differences between a signal of fluorescence intensity and a background of the fluorescence intensity;
(d) select the combination of the labeled molecule and the binding molecule based on a magnitude of a signal of fluorescence intensity;
(e) select the combination of the labeled molecule and the binding molecule so that labels are to be assigned in a descending order of the signal of fluorescence intensity to binding molecules in an ascending order of a value of the first signal group; and
(f) select the combination of the labeled molecule and the binding molecule so that labels are to be assigned in an ascending order of a length of a detection wavelength to binding molecules in a descending order of a value of the first signal group; and
wherein in each of the one or more selected methods from (a) to (f), the significance of the binding molecule and/or the labeled molecule with respect to the target molecule is estimated by determining whether or not to raise a luminance in accordance with a type of the binding molecule or the labeled molecule, considering how the threshold is to be set, and lowering a background to enable an object signal to be picked up more easily when the object signal is weak, and
a detection apparatus configured to detect the signal emitted from the target molecule labeled using the binding molecule which is selected based on the output reactivity and which is labeled by the labeled molecule.

* * * * *